(12) United States Patent
Lin et al.

(10) Patent No.: US 12,139,716 B2
(45) Date of Patent: Nov. 12, 2024

(54) COMPOSITION FOR EDITING A NUCLEIC ACID SEQUENCE AND METHOD USING THE SAME

(71) Applicants: Lung-Jr Lin, Taichung (TW); Yi-hua Hsu, Taipei (TW)

(72) Inventors: Lung-Jr Lin, Taichung (TW); Yi-hua Hsu, Taipei (TW)

( * ) Notice: Subject to any disclaimer, the term of this patent is extended or adjusted under 35 U.S.C. 154(b) by 1108 days.

(21) Appl. No.: 16/472,274

(22) PCT Filed: Dec. 20, 2017

(86) PCT No.: PCT/US2017/067484
§ 371 (c)(1),
(2) Date: Jun. 21, 2019

(87) PCT Pub. No.: WO2018/119021
PCT Pub. Date: Jun. 28, 2018

(65) Prior Publication Data
US 2019/0323019 A1    Oct. 24, 2019

Related U.S. Application Data

(60) Provisional application No. 62/437,347, filed on Dec. 21, 2016.

(51) Int. Cl.
*C12N 15/73* (2006.01)
*C12N 15/66* (2006.01)
*C12N 15/79* (2006.01)
*C12N 15/90* (2006.01)

(52) U.S. Cl.
CPC ............. *C12N 15/73* (2013.01); *C12N 15/66* (2013.01); *C12N 15/79* (2013.01); *C12N 15/907* (2013.01)

(58) Field of Classification Search
None
See application file for complete search history.

(56) References Cited

U.S. PATENT DOCUMENTS

| | | |
|---|---|---|
| 2004/0092016 A1 | 5/2004 | Court et al. |
| 2014/0134741 A1 | 5/2014 | Gregory et al. |
| 2015/0093824 A1 | 4/2015 | Satishchandran et al. |

OTHER PUBLICATIONS

International Search Report and Written Opinion dated May 1, 2018 in connection with PCT/US2017/067484.

*Primary Examiner* — Nancy J Leith
(74) *Attorney, Agent, or Firm* — BEHMKE INNOVATION GROUP LLC; James M. Behmke; James J. Wong

(57) ABSTRACT

Provided is a composition for simultaneously targeting a nucleic acid sequence and providing intron selection in cells in vitro, ex vivo or in vivo. The composition includes one or more nucleic acid molecules each including an artificial nucleic acid sequence flanked with capping sequences, and Lambda beta protein or a linear or circular vector including a nucleic acid sequence encoding the Lambda beta protein, wherein each of the capping sequences is homologous to a region in a target nucleic acid sequence, and the artificial nucleic acid sequence is an intron sequence. The present disclosure also provides a method for editing a target nucleic acid sequence in cells by introducing the composition into the cells.

16 Claims, 11 Drawing Sheets
Specification includes a Sequence Listing.

SEQUENCE LISTING

<160> NUMBER OF SEQ ID NOS: 41

<210> SEQ ID NO 1
<211> LENGTH: 9536
<212> TYPE: DNA
<213> ORGANISM: Artificial Sequence
<220> FEATURE:
<223> OTHER INFORMATION: pAB-mCherry

<400> SEQUENCE: 1

| | | | | | | |
|---|---|---|---|---|---|---|
| gacggatcgg | gagatctccc | gatcccctat | ggtgcactct | cagtacaatc | tgctctgatg | 60 |
| ccgcatagtt | aagccagtat | ctgctccctg | cttgtgtgtt | ggaggtcgct | gagtagtgcg | 120 |
| cgagcaaaat | ttaagctaca | acaaggcaag | gcttgaccga | caattgcatg | aagaatctgc | 180 |
| ttagggttag | gcgttttgcg | ctgcttcgcg | atgtacgggc | cagatatacg | cgttgacatt | 240 |
| gattattgac | tagttattaa | tagtaatcaa | ttacggggtc | attagttcat | agcccatata | 300 |
| tggagttccg | cgttacataa | cttacggtaa | atggcccgcc | tggctgaccg | cccaacgacc | 360 |
| cccgcccatt | gacgtcaata | atgacgtatg | ttcccatagt | aacgccaata | gggactttcc | 420 |
| attgacgtca | atgggtggag | tatttacggt | aaactgccca | cttggcagta | catcaagtgt | 480 |
| atcatatgcc | aagtacgccc | cctattgacg | tcaatgacgg | taaatggccc | gcctggcatt | 540 |
| atgcccagta | catgacctta | tgggactttc | ctacttggca | gtacatctac | gtattagtca | 600 |
| tcgctattac | catggtgatg | cggttttggc | agtacatcaa | tgggcgtgga | tagcggtttg | 660 |
| actcacgggg | atttccaagt | ctccacccca | ttgacgtcaa | tgggagtttg | ttttggcacc | 720 |
| aaaatcaacg | ggactttcca | aaatgtcgta | acaactccgc | cccattgacg | caaatgggcg | 780 |
| gtaggcgtgt | acggtgggag | gtctatataa | gcagagctct | ctggctaact | agagaaccca | 840 |
| ctgcttactg | gcttatcgaa | attaatacga | ctcactatag | ggagacccaa | gctggctagc | 900 |
| gtttaaactt | aagcttggta | ccgagctcgc | caccatgagt | actgcactcg | caacgctggc | 960 |
| tgggaagctg | gctgaacgtg | tcggcatgga | ttctgtcgac | ccacaggaac | tgatcaccac | 1020 |
| tcttcgccag | acggcattta | aggtgatgca | cagcgatgcg | cagttcatcg | cattactgat | 1080 |
| cgttgccaac | cagtacggcc | ttaatccgtg | gacgaaagaa | atttacgcct | tcctgataa | 1140 |
| gcagaatggc | atcgttccgg | tggtgggcgt | tgatggctgg | tcccgcatca | tcaatgaaaa | 1200 |
| ccagcagttt | gatggcatgg | actttgagca | ggacaatgaa | tcctgtacat | gccggattta | 1260 |
| ccgcaaggac | cgtaatcatc | cgatctgcgt | taccgaatgg | atggatgaat | gccgccgcga | 1320 |
| accattcaaa | actcgcgaag | gcagagaaat | cacggggccg | tggcagtcgc | atcccaaacg | 1380 |
| gatgttacgt | cataaagcca | tgattcagtg | tgcccgtctg | gccttcggat | tgctggtat | 1440 |
| ctatgacaag | gatgaagccg | agcgcattgt | cgaaaatact | gcatacactg | cagaacgtca | 1500 |
| gccggaacgc | gacatcactc | cggttaacga | tgaaaccatg | caggagatta | acactctgct | 1560 |
| gatcgccctg | gataaaacat | gggatgacga | cttattgccg | ctctgttccc | agatatttcg | 1620 |
| ccgcgacatt | cgtgcatcgt | cagaactgac | acaggccgaa | gcagtaaaag | ctcttggatt | 1680 |
| cctgaaacag | aaagccgcag | agcagaaggt | ggcagcatga | tagtgagatc | gcggccgca | 1740 |
| tagataactg | atccagtgtg | ctggaattaa | ttcgctgtct | gcgagggcca | gctgttgggg | 1800 |
| tgagtactcc | ctctcaaaag | cgggcatgac | ttctgcgcta | agattgtcag | tttccaaaaa | 1860 |
| cgaggaggat | ttgatattca | cctggcccgc | ggtgatgcct | ttgagggtgg | ccgcgtccat | 1920 |
| ctggtcagaa | aagacaatct | ttttgttgtc | aagcttgagg | tgtggcaggc | ttgagatctg | 1980 |
| gccatacact | tgagtgacaa | tgacatccac | tttgcctttc | tctccacagg | tgtccactcc | 2040 |

```
caggtccaac tgcaggtcga gcatgcatct agggcggcca attccgcccc tctcccccc   2100
acccctctcc ctcccccccc cctaacgtta ctggccgaag ccgcttggaa taaggccggt   2160
gtgcgtttgt ctatatgtta ttttccacca tattgccgtc ttttggcaat gtgagggccc   2220
ggaaacctgg ccctgtcttc ttgacgagca ttcctagggg tctttcccct ctcgccaaag   2280
gaatgcaagg tctgttgaat gtcgtgaagg aagcagttcc tctggaagct tcttgaagac   2340
aaacaacgtc tgtagcgacc ctttgcaggc agcggaaccc cccacctggc gacaggtgcc   2400
tctgcggcca aaagccacgt gtataagata cacctgcaaa ggcggcacaa ccccagtgcc   2460
acgttgtgag ttggatagtt gtggaaagag tcaaatggct ctcctcaagc gtattcaaca   2520
aggggctgaa ggatgcccag aaggtacccc attgtatggg atctgatctg gggcctcggt   2580
gcacatgctt tacatgtgtt tagtcgaggt taaaaaaacg tctaggcccc ccgaaccacg   2640
gggacgtggt tttcctttga aaaacacgat gataagcttg ccacaaccca caaggagacg   2700
accttccgcc accatgacac cggacattat cctgcagcgt accgggatcg atgtgagagc   2760
tgtcgaacag ggggatgatg cgtggcacaa attacggctc ggcgtcatca ccgcttcaga   2820
agttcacaac gtgatagcaa aaccccgctc cggaaagaag tggcctgaca tgaaaatgtc   2880
ctacttccac accctgcttg ctgaggtttg caccggtgtg gctccggaag ttaacgctaa   2940
agcactggcc tggggaaaac agtacgagaa cgacgccaga accctgtttg aattcacttc   3000
cggcgtgaat gttactgaat ccccgatcat ctatcgcgac gaaagtatgc gtaccgcctg   3060
ctctcccgat ggtttatgca gtgacggcaa cggccttgaa ctgaaatgcc cgtttacctc   3120
ccgggatttc atgaagttcc ggctcggtgg tttcgaggcc ataaagtcag cttacatggc   3180
ccaggtgcag tacagcatgt gggtgacgcg aaaaaatgcc tggtactttg ccaactatga   3240
cccgcgtatg aagcgtgaag gcctgcatta tgtcgtgatt gagcgggatg aaaagtacat   3300
ggcgagtttt gacgagatcg tgccggagtt catcgaaaaa atggacgagg cactggctga   3360
aattggtttt gtatttgggg agcaatggcg atgatctaga gatccgcggc cgcatagata   3420
actgatccag tgtgctggaa ttaattcgct gtctgcgagg gccagctgtt ggggtgagta   3480
ctccctctca aaagcgggca tgacttctgc gctaagattg tcagtttcca aaaacgagga   3540
ggatttgata ttcacctggc ccgcggtgat gcctttgagg gtggccgcgt ccatctggtc   3600
agaaaagaca atcttttgt tgtcaagctt gaggtgtggc aggcttgaga tctggccata   3660
cacttgagtg acaatgacat ccactttgcc tttctctcca caggtgtcca ctcccaggtc   3720
caactgcagg tcgagcatgc atctagggcg gccaattccg cccctctccc ccaccccct   3780
ctccctcccc cccctaac gttactggcc gaagccgctt ggaataaggc cggtgtgcgt   3840
ttgtctatat gttatttcc accatattgc cgtcttttgg caatgtgagg gcccggaaac   3900
ctggccctgt cttcttgacg agcattccta ggggtctttc cctctcgcc aaaggaatgc   3960
aaggtctgtt gaatgcgtg aaggaagcag ttcctctgga agcttcttga agacaaacaa   4020
cgtctgtagc gaccctttgc aggcagcgga acccccacc tggcgacagg tgcctctgcg   4080
gccaaaagcc acgtgtataa gatacacctg caaggcggc acaacccag tgccacgttg   4140
tgagttggat agtgtggaa agagtcaaat ggctctcctc aagcgtattc aacaaggggc   4200
tgaaggatgc ccagaaggta ccccattgta tgggatctga tctggggcct cggtgcacat   4260
gctttacatg tgtttagtcg aggttaaaaa aacgtctagg ccccccgaac cacggggacg   4320
tggttttcct ttgaaaaaca cgatgataag cttgccacaa cccacaagga gacgaccttc   4380
```

-continued

```
cgccaccatg gtgagcaagg gcgaggagga taacatggcc atcatcaagg agttcatgcg    4440
cttcaaggtg cacatggagg gctccgtgaa cggccacgag ttcgagatcg agggcgaggg    4500
cgagggccgc ccctacgagg gcacccagac cgccaagctg aaggtgacca agggtggccc    4560
cctgcccttc gcctgggaca tcctgtcccc tcagttcatg tacggctcca aggcctacgt    4620
gaagcacccc gccgacatcc ccgactactt gaagctgtcc ttccccgagg gcttcaagtg    4680
ggagcgcgtg atgaacttcg aggacggcgg cgtggtgacc gtgacccagg actcctccct    4740
gcaggacggc gagttcatct acaaggtgaa gctgcgcggc accaacttcc cctccgacgg    4800
ccccgtaatg cagaagaaga ccatgggctg ggaggcctcc tccgagcgga tgtaccccga    4860
ggacggcgcc ctgaagggcg agatcaagca gaggctgaag ctgaaggacg gcggccacta    4920
cgacgctgag gtcaagacca cctacaaggc caagaagccc gtgcagctgc ccggcgccta    4980
caacgtcaac atcaagttgg acatcacctc ccacaacgag gactacacca tcgtggaaca    5040
gtacgaacgc gccgagggcc gccactccac cggcggcatg gacagctgt acaagtaatc    5100
tagagggccc gtttaaaccc gctgatcagc ctcgactgtg ccttctagtt gccagccatc    5160
tgttgtttgc ccctccccg tgccttcctt gaccctggaa ggtgccactc ccactgtcct    5220
ttcctaataa aatgaggaaa ttgcatcgca ttgtctgagt aggtgtcatt ctattctggg    5280
gggtggggtg gggcaggaca gcaaggggga ggattgggaa gacaatagca ggcatgctgg    5340
ggatgcggtg ggctctatgg cttctgaggc ggaaagaacc agctggggct ctaggggta    5400
tccccacgcg ccctgtagcg gcgcattaag cgcggcgggt gtggtggtta cgcgcagcgt    5460
gaccgctaca cttgccagcg ccctagcgcc cgctcctttc gctttcttcc cttcctttct    5520
cgccacgttc gccggctttc cccgtcaagc tctaaatcgg gggctccctt tagggttccg    5580
atttagtgct ttacgcacc tcgaccccaa aaaacttgat tagggtgatg gttcacgtag    5640
tgggccatcg ccctgataga cggtttttcg ccctttgacg ttggagtcca cgttctttaa    5700
tagtggactc ttgttccaaa ctggaacaac actcaaccct atctcggtct attcttttga    5760
tttataaggg attttgccga tttcggccta ttggttaaaa aatgagctga tttaacaaaa    5820
atttaacgcg aattaattct gtggaatgtg tgtcagttag ggtgtggaaa gtccccaggc    5880
tccccagcag gcagaagtat gcaaagcatg catctcaatt agtcagcaac caggtgtgga    5940
aagtccccag gctccccagc aggcagaagt atgcaaagca tgcatctcaa ttagtcagca    6000
accatagtcc cgcccctaac tccgcccatc ccgccctaa ctccgcccag ttccgcccat    6060
tctccgcccc atggctgact aatttttttt atttatgcag aggccgaggc cgcctctgcc    6120
tctgagctat tccagaagta gtgaggaggc ttttttggag gcctaggctt ttgcaaaaag    6180
ctcccgggag cttgtatatc cattttcgga tctgatcaag agacaggatg aggatcgttt    6240
cgcatgattg aacaagatgg attgcacgca ggttctccgg ccgcttgggt ggagaggcta    6300
ttcggctatg actgggcaca acagacaatc ggctgctctg atgccgccgt gttccggctg    6360
tcagcgcagg ggcgcccggt tctttttgtc aagaccgacc tgtccggtgc cctgaatgaa    6420
ctgcaggacg aggcagcgcg gctatcgtgg ctggccacga cgggcgttcc ttgcgcagct    6480
gtgctcgacg ttgtcactga agcgggaagg gactggctgc tattgggcga agtgccgggg    6540
caggatctcc tgtcatctca ccttgctcct gccgagaaag tatccatcat ggctgatgca    6600
atgcggcggc tgcatacgct tgatccggct acctgcccat tcgaccacca agcgaaacat    6660
cgcatcgagc gagcacgtac tcggatggaa gccggtcttg tcgatcagga tgatctggac    6720
gaagagcatc aggggctcgc gccagccgaa ctgttcgcca ggctcaaggc gcgcatgccc    6780
```

-continued

```
gacggcgagg atctcgtcgt gacccatggc gatgcctgct tgccgaatat catggtggaa    6840
aatggccgct tttctggatt catcgactgt ggccggctgg gtgtggcgga ccgctatcag    6900
gacatagcgt tggctacccg tgatattgct gaagagcttg gcggcgaatg ggctgaccgc    6960
ttcctcgtgc tttacggtat cgccgctccc gattcgcagc gcatcgcctt ctatcgcctt    7020
cttgacgagt tcttctgagc gggactctgg ggttcgaaat gaccgaccaa gcgacgccca    7080
acctgccatc acgagatttc gattccaccg ccgccttcta tgaaaggttg gcttcggaa    7140
tcgtttccg ggacgccggc tggatgatcc tccagcgcgg ggatctcatg ctggagttct    7200
tcgcccaccc caacttgttt attgcagctt ataatggtta caaataaagc aatagcatca    7260
caaatttcac aaataaagca ttttttttcac tgcattctag ttgtggtttg tccaaactca    7320
tcaatgtatc ttatcatgtc tgtataccgt cgacctctag ctagagcttg gcgtaatcat    7380
ggtcatagct gtttcctgtg tgaaattgtt atccgctcac aattccacac aacatacgag    7440
ccggaagcat aaagtgtaaa gcctggggtg cctaatgagt gagctaactc acattaattg    7500
cgttgcgctc actgcccgct ttccagtcgg gaaacctgtc gtgccagctg cattaatgaa    7560
tcggccaacg cgcggggaga ggcggtttgc gtattgggcg ctcttccgct tcctcgctca    7620
ctgactcgct gcgctcggtc gttcggctgc ggcgagcggt atcagctcac tcaaaggcgg    7680
taatacggtt atccacagaa tcaggggata acgcaggaaa gaacatgtga gcaaaaggcc    7740
agcaaaaggc caggaaccgt aaaaaggccg cgttgctggc gttttttccat aggctccgcc    7800
cccctgacga gcatcacaaa aatcgacgct caagtcagag gtggcgaaac ccgacaggac    7860
tataaagata ccaggcgttt ccccctggaa gctccctcgt gcgctctcct gttccgaccc    7920
tgccgcttac cggatacctg tccgcctttc tcccttcggg aagcgtggcg ctttctcata    7980
gctcacgctg taggtatctc agttcggtgt aggtcgttcg ctccaagctg ggctgtgtgc    8040
acgaaccccc cgttcagccc gaccgctgcg ccttatccgg taactatcgt cttgagtcca    8100
acccggtaag acacgactta tcgccactgg cagcagccac tggtaacagg attagcagag    8160
cgaggtatgt aggcggtgct acagagttct tgaagtggtg gcctaactac ggctacacta    8220
gaagaacagt atttggtatc tgcgctctgc tgaagccagt taccttcgga aaaagagttg    8280
gtagctcttg atccggcaaa caaaccaccg ctggtagcgg ttttttttgtt tgcaagcagc    8340
agattacgcg cagaaaaaaa ggatctcaag aagatccttt gatctttctt acggggtctg    8400
acgctcagtg gaacgaaaac tcacgttaag ggattttggt catgagatta tcaaaaagga    8460
tcttcaccta gatcctttta aattaaaaat gaagttttaa atcaatctaa agtatatatg    8520
agtaaacttg gtctgacagt taccaatgct taatcagtga ggcacctatc tcagcgatct    8580
gtctatttcg ttcatccata gttgcctgac tccccgtcgt gtagataact acgatacggg    8640
agggcttacc atctggcccc agtgctgcaa tgataccgcg agacccacgc tcaccggctc    8700
cagatttatc agcaataaac cagccagccg gaagggccga gcgcagaagt ggtcctgcaa    8760
ctttatccgc ctccatccag tctattaatt gttgccggga agctagagta agtagttcgc    8820
cagttaatag tttgcgcaac gttgttgcca ttgctacagg catcgtggtg tcacgctcgt    8880
cgtttggtat ggcttcattc agctccggtt cccaacgatc aaggcgagtt acatgatccc    8940
ccatgttgtg caaaaaagcg gttagctcct tcggtcctcc gatcgttgtc agaagtaagt    9000
tggccgcagt gttatcactc atggttatgg cagcactgca taattctctt actgtcatgc    9060
catccgtaag atgcttttct gtgactggtg agtactcaac caagtcattc tgagaatagt    9120
```

-continued

| | |
|---|---|
| gtatgcggcg accgagttgc tcttgcccgg cgtcaatacg ggataatacc gcgccacata | 9180 |
| gcagaacttt aaaagtgctc atcattggaa aacgttcttc ggggcgaaaa ctctcaagga | 9240 |
| tcttaccgct gttgagatcc agttcgatgt aacccactcg tgcacccaac tgatcttcag | 9300 |
| catcttttac tttcaccagc gtttctgggt gagcaaaaac aggaaggcaa aatgccgcaa | 9360 |
| aaaagggaat aagggcgaca cggaaatgtt gaatactcat actcttcctt tttcaatatt | 9420 |
| attgaagcat ttatcagggt tattgtctca tgagcggata catatttgaa tgtatttaga | 9480 |
| aaaataaaca aatagggtt ccgcgcacat ttccccgaaa agtgccacct gacgtc | 9536 |

<210> SEQ ID NO 2
<211> LENGTH: 5728
<212> TYPE: DNA
<213> ORGANISM: Artificial Sequence
<220> FEATURE:
<223> OTHER INFORMATION: pAF-INTRON

<400> SEQUENCE: 2

| | |
|---|---|
| ctcgaggtaa gttaggcagg gatattcacc attatcgttt cagacccacc tcccaacccc | 60 |
| gaggggaccc gacaggcccg aaggaataga agaagaaggt ggagagagag acagagacag | 120 |
| atccattcga ttagtgaacg gatctcgacg gtatcgatac tagtattatg cccagtacat | 180 |
| gaccttatgg gactttccta cttggcagta catctacgta ttagtcatcg ctattaccat | 240 |
| ggtgatgcgg ttttggcagt acatcaatgg gcgtggatag cggtttgact cacggggatt | 300 |
| tccaagtctc cacccattg acgtcaatgg gagtttgttt tggcaccaaa atcaacggga | 360 |
| ctttccaaaa tgtcgtaaca actccgcccc attgacgcaa atgggcggta ggcgtgtacg | 420 |
| gtgggaggtc tatataagca gagctcgttt agtgaaccgt cagatcgcct ggagacgcca | 480 |
| tccacgctgt tttgacctcc atagaagatt ctagaaccat ggctagcgtg agcaagggcg | 540 |
| aggagctgtt caccggggtg gtgcccatcc tggtcgagct ggacggcgac gtaaacggcc | 600 |
| acaagttcag cgtgtccggc gagggcgagg gcgatgccac ctacggcaag ctgaccctga | 660 |
| agttcatctg caccaccggc aagctgcccg tgccctggcc caccctcgtg accaccctga | 720 |
| cctacggcgt gcagtgcttc agccgctacc ccgaccacat gaagcagcac gacttcttca | 780 |
| agtccgccat gcccgaaggc tacgtccagg agcgcaccat cttcttcaag gacgacggca | 840 |
| actacaagac ccgcgccgag gtgaagttcg agggcgacac cctggtgaac cgcatcgagc | 900 |
| tgaagggcat cgacttcaag gaggacggca acatcctggg gcacaagctg gagtacaact | 960 |
| acaacagcca caacgtctat atcatggccg acaagcagaa gaacggcatc aaggtgaact | 1020 |
| tcaagatccg ccacaacatc gaggacggca gcgtgcagct cgccgaccac taccagcaga | 1080 |
| acaccccat cggcgacggc cccgtgctgc tgcccgacaa ccactacctg agcacccagt | 1140 |
| ccgccctgag caaagacccc aacgagaagc gcgatcacat ggtcctgctg gagttcgtga | 1200 |
| ccgccgccgg gatcactctc ggcatggacg agctgtacaa gtgatccgtt caactagcag | 1260 |
| accgtttaaa caattcaagc ttttttcaat tctcgacctc gagacaaatg gcagtattca | 1320 |
| tccacaattt taaaagaaaa ggggggattg ggggtacag tgcaggggaa agaatagtag | 1380 |
| acataatagc aacagacata caaactaaag aattacaaaa acaaattaca aaaattcaaa | 1440 |
| attttcgggt ttattacagg gacagcagag atccagtttg gccgcggctc gaggggggttg | 1500 |
| gggttgcgcc ttttccaagg cagccctggg tttgcgcagg gacgcggctg ctctgggcgt | 1560 |
| ggttccggga aacgcagcgg cgccgaccct gggtctcgca cattcttcac gtccgttcgc | 1620 |
| agcgtcaccc ggatcttcgc cgctacccct tgtgggcccc cggcgacgct tcctgctccg | 1680 |

-continued

```
cccctaagtc gggaaggttc cttgcggttc gcggcgtgcc ggacgtgaca aacggaagcc   1740
gcacgtctca ctagtaccct cgcagacgga cagcgccagg gagcaatggc agcgcgccga   1800
ccgcgatggg ctgtggccaa tagcggctgc tcagcagggc gcgccgagag cagcggccgg   1860
gaaggggcgg tgcgggaggc ggggtgtggg gcggtagtgt gggccctgtt cctgcccgcg   1920
cggtgttccg cattctgcaa gcctccggag cgcacgtcgg cagtcggctc cctcgttgac   1980
cgaatcaccg acctctctcc caggggat ccaccggagc ttaccatgac cgagtacaag    2040
cccacggtgc gcctcgccac ccgcgacgac gtccccaggg cggtacgcac cctcgccgcc   2100
gcgttcgccg actaccccgc cacgcgccac accgtcgatc cggaccgcca catcgagcgg   2160
gtcaccgagc tgcaagaact cttcctcacg cgcgtcgggc tcgacatcgg caaggtgtgg   2220
gtcgcggacg acgcgccgc ggtggcggtc tggaccacgc cggagagcgt cgaagcgggg    2280
gcggtgttcg ccgagatcgg cccgcgcatg gccgagttga gcggttcccg gctggccgcg   2340
cagcaacaga tggaaggcct cctggcgccg caccggccca aggagcccgc gtggttcctg   2400
gccaccgtcg gcgtctcgcc cgaccaccag ggcaagggtc tgggcagcgc cgtcgtgctc   2460
cccggagtgg aggcggccga gcgcgccggg gtgcccgcct tcctggagac ctccgcgccc   2520
cgcaacctcc ccttctacga gcggctcggc ttcaccgtca ccgccgacgt cgaggtgccc   2580
gaaggaccgc gcacctggtg catgacccgc aagcccggtg cctgacgccc gccccacgac   2640
ccgcagcgcc cgaccgaaag gagcgcacga ccccatgcat cgttaagagc tcggtacctt   2700
taagaccaat gacttacaag gcagctgtag atcttagcca cttttaaaa gaaaagggg    2760
gactggaagg gctaattcac tcccaacgaa gacaagatct gcttttgct tgtactgggt    2820
ctctctggtt agaccagatc tgagcctggg agctctctcg ctaactaggg aacccactgc   2880
ttaagcctca ataaagcttg ccttgagtgc ttcaagtagt gtgtgcccgt ctgttgtgtg   2940
actctggtaa ctagagatcc ctcagaccct tttagtcagt gtggaaaatc tctagcagta   3000
gtagttcatg tcatcttatt attcagtatt tataacttgc aaagaaatga atatcagaga   3060
gtgagaggaa cttgtttatt gcagcttata atggttacaa ataaagcaat agcatcacaa   3120
atttcacaaa taaagcattt ttttcactgc attctagttg tggtttgtcc aaactcatca   3180
atgtatctta tcatgtctgg ctctagctat cccgccccta actccgccca tcccgcccct   3240
aactccgccc agttccgccc attctccgcc ccatggctga ctaattttt ttatttatgc    3300
agacgcctgg ggtaatgact ctctagcttg aggcatcaaa taaaacgaaa ggctcagtcg   3360
aaagactggg cctttcgttt tatctgttgt ttgtcggtga acgctctcct gagtaggaca   3420
aatccgccct ctagagctgc ctcgcgcgtt tcggtgatga cggtgaaaac ctctgacaca   3480
tgcagctccc ggagacggtc acagcttgtc tgtaagcgga tgccgggagc agacaagccc   3540
gtcagggcgc gtcagcgggt gttggcgggt gtcggggcgc agccatgacc cagtcacgta   3600
gcgatagcgg agtgtatact ggcttaacta tgcggcatca gagcagattg tactgagagt   3660
gcggccgctg cggtgtgaaa taccgcacag atgcgtaagg agaaaatacc gcatcaggcg   3720
ctcttccgct tcctcgctca ctgactcgct gcgctcggtc gttcggctgc ggcgagcggt   3780
atcagctcac tcaaaggcgg taatacggtt atccacagaa tcaggggata acgcaggaaa   3840
gaacatgtga gcaaaaggcc agcaaaaggc caggaaccgt aaaaaggccg cgttgctggc   3900
gttttccat aggctccgcc cccctgacga gcatcacaaa aatcgacgct caagtcagag    3960
gtggcgaaac ccgacaggac tataaagata ccaggcgttt ccccctggaa gctccctcgt   4020
```

-continued

```
gcgctctcct gttccgaccc tgccgcttac cggatacctg tccgccttc tcccttcggg    4080
aagcgtggcg ctttctcata gctcacgctg taggtatctc agttcggtgt aggtcgttcg    4140
ctccaagctg ggctgtgtgc acgaaccccc cgttcagccc gaccgctgcg ccttatccgg    4200
taactatcgt cttgagtcca acccggtaag acacgactta tcgccactgg cagcagccac    4260
tggtaacagg attagcagag cgaggtatgt aggcggtgct acagagttct tgaagtggtg    4320
gcctaactac ggctacacta aaggacagt atttggtatc tgcgctctgc tgaagccagt     4380
taccttcgga aaagagttg gtagctcttg atccggcaaa caaaccaccg ctggtagcgg     4440
tggttttttt gtttgcaagc agcagattac gcgcagaaaa aaggatctc aagaagatcc     4500
tttgatcttt tctacggggt ctgacgctca gtggaacgaa aactcacgtt aagggatttt    4560
ggtcatgaga ttatcaaaaa ggatcttcac ctagatcctt ttaaattaaa aatgaagttt    4620
taaatcaatc taaagtatat atgagtaaac ttggtctgac agttaccaat gcttaatcag    4680
tgaggcacct atctcagcga tctgtctatt tcgttcatcc atagttgcct gactccccgt    4740
cgtgtagata actacgatac gggagggctt accatctggc cccagtgctg caatgatacc    4800
gcgagaccca cgctcaccgg ctccagattt atcagcaata aaccagccag ccggaagggc    4860
cgagcgcaga agtggtcctg caactttatc cgcctccatc cagtctatta attgttgccg    4920
ggaagctaga gtaagtagtt cgccagttaa tagtttgcgc aacgttgttg ccattgctac    4980
aggcatcgtg gtgtcacgct cgtcgtttgg tatggcttca ttcagctccg gttcccaacg    5040
atcaaggcga gttacatgat cccccatgtt gtgcaaaaaa gcggttagct ccttcggtcc    5100
tccgatcgtt gtcagaagta agttggccgc agtgttatca ctcatggtta tggcagcact    5160
gcataattct cttactgtca tgccatccgt aagatgcttt tctgtgactg gtgagtactc    5220
aaccaagtca ttctgagaat agtgtatgcg gcgaccgagt tgctcttgcc cggcgtcaat    5280
acgggataat accgcgccac atagcagaac tttaaaagtg ctcatcattg gaaaacgttc    5340
ttcggggcga aaactctcaa ggatcttacc gctgttgaga tccagttcga tgtaacccac    5400
tcgtgcaccc aactgatctt cagcatcttt tactttcacc agcgtttctg ggtgagcaaa    5460
aacaggaagg caaaatgccg caaaaaaggg aataagggcg acacggaaat gttgaatact    5520
catactcttc ctttttcaat attattgaag catttatcag ggttattgtc tcatgagcgg    5580
atacatattt gaatgtattt agaaaaataa acaaataggg gttccgcgca catttccccg    5640
aaaagtgcca cctgacgtct aagaaaccat tattatcatg acattaacct ataaaaatag    5700
gcgtatcacg aggccctttc gtcttcac                                       5728
```

<210> SEQ ID NO 3
<211> LENGTH: 322
<212> TYPE: DNA
<213> ORGANISM: Homo sapiens
<220> FEATURE:
<221> NAME/KEY: exon
<222> LOCATION: (1)..(322)

<400> SEQUENCE: 3

```
agc aaa ccg ccc aga gta gaa gat gga ttg ggg cac gct gca gac gat      48
Ser Lys Pro Pro Arg Val Glu Asp Gly Leu Gly His Ala Ala Asp Asp
1               5                   10                  15 cct ggg ggg tgt gaa caa aca ctc cac cag cat tgg aaa gat ctg gct      96
Pro Gly Gly Cys Glu Gln Thr Leu His Gln His Trp Lys Asp Leu Ala
            20                  25                  30 cac cgt cct ctt cat ttt tcg cat tat gat cct cgt tgt ggc tgc aaa     144
His Arg Pro Leu His Phe Ser His Tyr Asp Pro Arg Cys Gly Cys Lys
```

```
                 35                  40                  45
gga ggt gtg ggg aga tga gca ggc cga ctt tgt ctg caa cac cct gca    192
Gly Gly Val Gly Arg     Ala Gly Arg Leu Cys Leu Gln His Pro Ala
         50                  55                  60 gcc agg ctg caa gaa cgt gtg cta cga tca cta ctt ccc cat ctc cca    240
Ala Arg Leu Gln Glu Arg Val Leu Arg Ser Leu Leu Pro His Leu Pro
 65                  70                  75 cat ccg gct atg ggc cct gca gct gat ctt cgt gtc cac gcc agc gct    288
His Pro Ala Met Gly Pro Ala Ala Asp Leu Arg Val His Ala Ser Ala
 80                  85                  90                  95 cct agt ggc cat gca cgt ggc cta ccg gag aca t                      322
Pro Ser Gly His Ala Arg Gly Leu Pro Glu Thr
                100                 105

<210> SEQ ID NO 4
<211> LENGTH: 321
<212> TYPE: DNA
<213> ORGANISM: Homo sapiens
<220> FEATURE:
<221> NAME/KEY: exon
<222> LOCATION: (1)..(321)

<400> SEQUENCE: 4 agc aaa ccg ccc aga gta gaa gat gga ttg ggg cac gct gca gac gat    48
Ser Lys Pro Pro Arg Val Glu Asp Gly Leu Gly His Ala Ala Asp Asp
 1               5                  10                  15 cct ggg ggt gtg aac aaa cac tcc acc agc att gga aag atc tgg ctc    96
Pro Gly Gly Val Asn Lys His Ser Thr Ser Ile Gly Lys Ile Trp Leu
             20                  25                  30 acc gtc ctc ttc att ttt cgc att atg atc ctc gtt gtg gct gca aag    144
Thr Val Leu Phe Ile Phe Arg Ile Met Ile Leu Val Val Ala Ala Lys
         35                  40                  45 gag gtg tgg gga gat gag cag gcc gac ttt gtc tgc aac acc ctg cag    192
Glu Val Trp Gly Asp Glu Gln Ala Asp Phe Val Cys Asn Thr Leu Gln
 50                  55                  60 cca ggc tgc aag aac gtg tgc tac gat cac tac ttc ccc atc tcc cac    240
Pro Gly Cys Lys Asn Val Cys Tyr Asp His Tyr Phe Pro Ile Ser His
 65                  70                  75                  80 atc cgg cta tgg gcc ctg cag ctg atc ttc gtg tcc acg cca gcg ctc    288
Ile Arg Leu Trp Ala Leu Gln Leu Ile Phe Val Ser Thr Pro Ala Leu
             85                  90                  95 cta gtg gcc atg cac gtg gcc tac cgg aga cat                        321
Leu Val Ala Met His Val Ala Tyr Arg Arg His
                100                 105

<210> SEQ ID NO 5
<211> LENGTH: 322
<212> TYPE: DNA
<213> ORGANISM: Homo sapiens
<220> FEATURE:
<221> NAME/KEY: exon
<222> LOCATION: (1)..(322)

<400> SEQUENCE: 5 agc aaa ccg ccc aga gta gaa gat gga ttg ggg cac gct gca gac gat    48
Ser Lys Pro Pro Arg Val Glu Asp Gly Leu Gly His Ala Ala Asp Asp
 1               5                  10                  15 cct ggg ggg tgt gaa caa aca ctc cac cag cat tgg aaa gat ctg gct    96
Pro Gly Gly Cys Glu Gln Thr Leu His Gln His Trp Lys Asp Leu Ala
             20                  25                  30 cac cgt cct ctt cat ttt tcg cat tat gat cct cat tgt ggc tgc aaa    144
His Arg Pro Leu His Phe Ser His Tyr Asp Pro His Cys Gly Cys Lys
         35                  40                  45
```

```
gga ggt gtg ggg aga tga gca ggc cga ctt tgt ctg caa cac cct gca      192
Gly Gly Val Gly Arg     Ala Gly Arg Leu Cys Leu Gln His Pro Ala
 50              55                  60 gcc agg ctg caa gaa cgt gtg cta cga tca cta ctt ccc cat ctc cca      240
Ala Arg Leu Gln Glu Arg Val Leu Arg Ser Leu Leu Pro His Leu Pro
 65              70                  75 cat ccg gct atg ggc cct gca gct gat ctt cgt gtc cac gcc agc gct      288
His Pro Ala Met Gly Pro Ala Ala Asp Leu Arg Val His Ala Ser Ala
 80              85              90                  95 cct agt ggc cat gca cgt ggc cta ccg gag aca t                         322
Pro Ser Gly His Ala Arg Gly Leu Pro Glu Thr
                100              105
```

<210> SEQ ID NO 6
<211> LENGTH: 3815
<212> TYPE: DNA
<213> ORGANISM: Artificial Sequence
<220> FEATURE:
<223> OTHER INFORMATION: GJB2-EX-AF
<220> FEATURE:
<221> NAME/KEY: prim_transcript
<222> LOCATION: (1)..(3815)

<400> SEQUENCE: 6

```
ggggtgcggt taaaaggcgc cacggcggga gacaggtgtt gcggccccgc agcgcccgcg      60
cgctcctctc cccgactcgg agccctcgg cggcgcccgg cccaggaccc gcctaggagc     120
gcaggagccc cagcgcagag accccaacgc cgagaccccc gccccggccc gccgcgcgtt    180
cctcccgacg caggtaggta agttaggcag ggatattcac cattatcgtt tcagacccac    240
ctcccaaccc cgaggggacc cgacaggccc gaaggaatag aagaagaagg tggagagaga    300
gacagagaca gatccattcg attagtgaac ggatctcgac ggtatcgata ctagtattat    360
gcccagtaca tgaccttatg ggactttcct acttggcagt acatctacgt attagtcatc    420
gctattacca tggtgatgcg gttttggcag tacatcaatg ggcgtggata gcggtttgac    480
tcacggggat ttccaagtct ccaccccatt gacgtcaatg ggagtttgtt ttggcaccaa    540
aatcaacggg actttccaaa atgtcgtaac aactccgccc cattgacgca aatgggcggt    600
aggcgtgtac ggtgggaggt ctatataagc agagctcgtt tagtgaaccg tcagatcgcc    660
tggagacgcc atccacgctg ttttgacctc catagaagat tctagaacca tggctagcgt    720
gagcaagggc gaggagctgt tcaccggggt ggtgcccatc ctggtcgagc tggacggcga    780
cgtaaacggc cacaagttca gcgtgtccgg cgagggcgag ggcgatgcca cctacggcaa    840
gctgaccctg aagttcatct gcaccaccgg caagctgccc gtgccctggc ccaccctcgt    900
gaccaccctg acctacggcg tgcagtgctt cagccgctac cccgaccaca tgaagcagca    960
cgacttcttc aagtccgcca tgcccgaagg ctacgtccag gagcgcacca tcttcttcaa   1020
ggacgacggc aactacaaga cccgcgccga ggtgaagttc gagggcgaca ccctggtgaa   1080
ccgcatcgag ctgaagggca tcgacttcaa ggaggacggc aacatcctgg ggcacaagct   1140
ggagtacaac tacaacagcc acaacgtcta tatcatggcc gacaagcaga agaacggcat   1200
caaggtgaac ttcaagatcc gccacaacat cgaggacggc agcgtgcagc tcgccgacca   1260
ctaccagcag aacaccccca tcggcgacgg ccccgtgctg ctgcccgaca ccactacct   1320
gagcacccag tccgccctga gcaaagaccc caacgagaag cgcgatcaca tggtcctgct   1380
ggagttcgtg accgccgccg ggatcactct cggcatggac gagctgtaca agtgatccgt   1440
tcaactagca gaccgtttaa acaattcaag cttttttcaa ttctcgacct cgagacaaat   1500
```

```
ggcagtattc atccacaatt ttaaaagaaa aggggggatt ggggggtaca gtgcagggga    1560
aagaatagta gacataatag caacagacat acaaactaaa gaattacaaa aacaaattac    1620
aaaaattcaa aattttcggg tttattacag ggacagcaga gatccagttt ggccgcggct    1680
cgagggggtt ggggttgcgc cttttccaag gcagccctgg gtttgcgcag ggacgcggct    1740
gctctgggcg tggttccggg aaacgcagcg cgccgaccc tgggtctcgc acattcttca    1800
cgtccgttcg cagcgtcacc cggatcttcg ccgctaccct tgtgggcccc ccggcgacgc    1860
ttcctgctcc gccoctaagt cgggaaggtt ccttgcggtt cgcggcgtgc cggacgtgac    1920
aaacggaagc cgcacgtctc actagtaccc tcgcagacgg acagcgccag ggagcaatgg    1980
cagcgcgccg accgcgatgg gctgtggcca atagcggctg ctcagcaggg cgcgccgaga    2040
gcagcggccg ggaaggggcg tgcgggagg cgggtgtgg ggcggtagtg tgggccctgt    2100
tcctgcccgc gcggtgttcc gcattctgca agcctccgga gcgcacgtcg gcagtcggct    2160
ccctcgttga ccgaatcacc gacctctctc cccaggggga tccaccggag cttaccatga    2220
ccgagtacaa gcccacggtg cgcctcgcca cccgcgacga cgtccccagg gcggtacgca    2280
ccctcgccgc cgcgttcgcc gactaccccg ccacgcgcca caccgtcgat ccggaccgcc    2340
acatcgagcg ggtcaccgag ctgcaagaac tcttcctcac gcgcgtcggg ctcgacatcg    2400
gcaaggtgtg ggtcgcggac gacggcgccg cggtggcggt ctggaccacg ccggagagcg    2460
tcgaagcggg ggcggtgttc gccgagatcg gcccgcgcat ggccgagttg agcggttccc    2520
ggctggccgc gcagcaacag atggaaggcc tcctggcgcc gcaccggccc aaggagcccg    2580
cgtggttcct ggccaccgtc ggcgtctcgc ccgaccacca gggcaagggt ctgggcagcg    2640
ccgtcgtgct ccccggagtg gaggcggccg agcgcgccgg ggtgcccgcc ttcctggaga    2700
cctccgcgcc ccgcaacctc cccttctacg agcggctcgg cttcaccgtc accgccgacg    2760
tcgaggtgcc cgaaggaccg cgcacctggt gcatgacccg caagcccggt gcctgacgcc    2820
cgccccacga cccgcagcgc ccgaccgaaa ggagcgcacg accccatgca tcgttaagag    2880
ctcggtacct ttaagaccaa tgacttacaa ggcagctgta gatcttagcc acttttaaaa    2940
agaaaagggg ggactggaag ggctaattca ctcccaacga agacaagatc tgcttttgc    3000 ttgtactggg tctctctggt tagaccagat ctgagcctgg gagctctctc gctaactagg    3060
gaacccactg cttaagcctc aataaagctt gccttgagtg cttcaagtag tgtgtgcccg    3120
tctgttgtgt gactctggta actagagatc cctcagaccc ttttagtcag tgtggaaaat    3180
ctctagcagt agtagttcat gtcatcttat tattcagtat ttataacttg caaagaaatg    3240
aatatcagag agtgagagga acttgtttat tgcagcttat aatggttaca aataaagcaa    3300
tagcatcaca aatttcacaa ataaagcatt ttttcactg cattctagtt gtggtttgtc    3360
caaactcatc aatgtatctt atcatgtctg gctctagcta tcccgcccct aactccgccc    3420
atcccgcccc taactccgcc cagttccgcc cattctccgc cccatggctg actaattttt    3480
tttatttatg cagagcaaac cgcccagagt agaagatgga ttggggcacg ctgcagacga    3540
tcctgggggg tgtgaacaaa cactccacca gcattggaaa gatctggctc accgtcctct    3600 tcattttcg cattatgatc ctcgttgtgg ctgcaaagga ggtgtggga gatgagcagg    3660 ccgactttgt ctgcaacacc ctgcagccag gctgcaagaa cgtgtgctac gatcactact    3720
tccccatctc ccacatccgg ctatgggccc tgcagctgat cttcgtgtcc acgccagcgc    3780
tcctagtggc catgcacgtg gcctaccgga gacat                              3815
```

<210> SEQ ID NO 7
<211> LENGTH: 3814
<212> TYPE: DNA
<213> ORGANISM: Artificial Sequence
<220> FEATURE:
<223> OTHER INFORMATION: GJB2-EX35-AF
<220> FEATURE:
<221> NAME/KEY: prim_transcript
<222> LOCATION: (1)..(3814)

<400> SEQUENCE: 7

```
ggggtgcggt taaaaggcgc cacggcggga gacaggtgtt gcggccccgc agcgcccgcg      60
cgctcctctc cccgactcgg agcccctcgg cggcgcccgg cccaggaccc gcctaggagc     120
gcaggagccc cagcgcagag accccaacgc cgagaccccc gccccggccc cgccgcgctt     180
cctcccgacg caggtaggta agttaggcag ggatattcac cattatcgtt tcagacccac     240
ctcccaaccc cgaggggacc cgacaggccc gaaggaatag aagaagaagg tggagagaga     300
gacagagaca gatccattcg attagtgaac ggatctcgac ggtatcgata ctagtattat     360
gcccagtaca tgaccttatg gactttcct acttggcagt acatctacgt attagtcatc      420
gctattacca tggtgatgcg gttttggcag tacatcaatg ggcgtggata gcggtttgac     480
tcacggggat ttccaagtct ccaccccatt gacgtcaatg ggagtttgtt ttggcaccaa     540
aatcaacggg actttccaaa atgtcgtaac aactccgccc cattgacgca aatgggcggt     600
aggcgtgtac ggtgggaggt ctatataagc agagctcgtt tagtgaaccg tcagatcgcc     660
tggagacgcc atccacgctg ttttgacctc catagaagat tctagaacca tggctagcgt     720
gagcaagggc gaggagctgt tcaccggggt ggtgcccatc ctggtcgagc tggacggcga     780
cgtaaacggc cacaagttca gcgtgtccgg cgagggcgag ggcgatgcca cctacggcaa     840
gctgaccctg aagttcatct gcaccaccgg caagctgccc gtgccctggc ccaccctcgt     900
gaccaccctg acctacggcg tgcagtgctt cagccgctac cccgaccaca tgaagcagca     960
cgacttcttc aagtccgcca tgcccgaagg ctacgtccag gagcgcacca tcttcttcaa    1020
ggacgacggc aactacaaga cccgcgccga ggtgaagttc gagggcgaca ccctggtgaa    1080
ccgcatcgag ctgaagggca tcgacttcaa ggaggacggc aacatcctgg ggcacaagct    1140
ggagtacaac tacaacagcc acaacgtcta tatcatggcc gacaagcaga agaacggcat    1200
caaggtgaac ttcaagatcc gccacaacat cgaggacggc agcgtgcagc tcgccgacca    1260
ctaccagcag aacacccca tcggcgacgg ccccgtgctg ctgcccgaca accactacct    1320
gagcacccag tccgccctga gcaaagaccc caacgagaag cgcgatcaca tggtcctgct    1380
ggagttcgtg accgccgccg ggatcactct cggcatggac gagctgtaca agtgatccgt    1440
tcaactagca gaccgtttaa acaattcaag ctttttcaa ttctcgacct cgagacaaat    1500
ggcagtattc atccacaatt ttaaaagaaa agggggggatt ggggggtaca gtgcagggga    1560
aagaatagta gacataatag caacagacat acaaactaaa gaattacaaa aacaaattac    1620
aaaaattcaa aattttcggg tttattacag ggacagcaga gatccagttt ggccgcggct    1680
cgaggggggtt ggggttgcgc cttttccaag gcagccctgg gtttgcgcag gacgcggct     1740
gctctgggcg tggttccggg aaacgcagcg cgccgaccc tggtctcgc acattcttca    1800
cgtccgttcg cagcgtcacc cggatcttcg ccgctaccct tgtgggcccc ccggcgacgc    1860
ttcctgctcc gccccctaagt cgggaaggtt ccttgcggtt cgcggcgtgc cggacgtgac    1920
aaacggaagc cgcacgtctc actagtaccc tcgcagacgg acagcgccag ggagcaatgg    1980
```

```
cagcgcgccg accgcgatgg gctgtggcca atagcggctg ctcagcaggg cgcgccgaga    2040
gcagcggccg ggaaggggcg gtgcgggagg cggggtgtgg ggcggtagtg tgggccctgt    2100
tcctgcccgc gcggtgttcc gcattctgca agcctccgga gcgcacgtcg gcagtcggct    2160
ccctcgttga ccgaatcacc gacctctctc cccaggggga tccaccggag cttaccatga    2220
ccgagtacaa gcccacggtg cgcctcgcca cccgcgacga cgtccccagg gcggtacgca    2280
ccctcgccgc cgcgttcgcc gactaccccg ccacgcgcca caccgtcgat ccggaccgcc    2340
acatcgagcg ggtcaccgag ctgcaagaac tcttcctcac gcgcgtcggg ctcgacatcg    2400
gcaaggtgtg ggtcgcggac gacggcgccg cggtggcggt ctggaccacg ccggagagcg    2460
tcgaagcggg ggcggtgttc gccgagatcg gcccgcgcat ggccgagttg agcggttccc    2520
ggctggccgc gcagcaacag atggaaggcc tcctggcgcc gcaccggccc aaggagcccg    2580
cgtggttcct ggccaccgtc ggcgtctcgc ccgaccacca gggcaagggt ctgggcagcg    2640
ccgtcgtgct ccccgagtg gaggcggccg agcgcgccgg ggtgcccgcc ttcctggaga    2700
cctccgcgcc ccgcaacctc cccttctacg agcggctcgg cttcaccgtc accgccgacg    2760
tcgaggtgcc cgaaggaccg cgcacctggt gcatgacccg caagcccggt gcctgacgcc    2820
cgccccacga cccgcagcgc ccgaccgaaa ggagcgcacg accccatgca tcgttaagag    2880
ctcggtacct ttaagaccaa tgacttacaa ggcagctgta gatcttagcc acttttttaaa   2940 agaaaagggg ggactggaag ggctaattca ctcccaacga agacaagatc tgcttttttgc   3000 ttgtactggg tctctctggt tagaccagat ctgagcctgg gagctctctc gctaactagg    3060
gaacccactg cttaagcctc aataaagctt gccttgagtg cttcaagtag tgtgtgcccg    3120
tctgttgtgt gactctggta actagagatc cctcagaccc ttttagtcag tgtggaaaat    3180
ctctagcagt agtagttcat gtcatcttat tattcagtat ttataacttg caaagaaatg    3240
aatatcagag agtgagagga acttgtttat tgcagcttat aatggttaca aataaagcaa    3300
tagcatcaca aatttcacaa ataaagcatt ttttcactg cattctagtt gtggtttgtc     3360
caaactcatc aatgtatctt atcatgtctg gctctagcta tcccgcccct aactccgccc    3420
atcccgcccc taactccgcc cagttccgcc cattctccgc cccatggctg actaattttt    3480
tttatttatg cagagcaaac cgcccagagt agaagatgga ttggggcacg ctgcagacga    3540
tcctgggggt gtgaacaaac actccaccag cattggaaag atctggctca ccgtcctctt    3600 cattttcgc attatgatcc tcgttgtggc tgcaaaggag gtgtggggag atgagcaggc     3660
cgactttgtc tgcaacaccc tgcagccagg ctgcaagaac gtgtgctacg atcactactt    3720
ccccatctcc cacatccggc tatgggccct gcagctgatc ttcgtgtcca cgccagcgct    3780
cctagtggcc atgcacgtgg cctaccggag acat                                3814
```

<210> SEQ ID NO 8
<211> LENGTH: 3815
<212> TYPE: DNA
<213> ORGANISM: Artificial Sequence
<220> FEATURE:
<223> OTHER INFORMATION: GJB2-EX109-AF
<220> FEATURE:
<221> NAME/KEY: prim_transcript
<222> LOCATION: (1)..(3815)

<400> SEQUENCE: 8

```
ggggtgcggt taaaaggcgc cacggcggga gacaggtgtt gcggcccgc agcgcccgcg      60 cgctcctctc cccgactcgg agcccctcgg cggcgcccgg cccaggaccc gcctaggagc    120
```

```
gcaggagccc cagcgcagag accccaacgc cgagaccccc gccccggccc cgccgcgctt      180
cctcccgacg caggtaggta agttaggcag ggatattcac cattatcgtt tcagacccac      240
ctcccaaccc cgaggggacc cgacaggccc gaaggaatag aagaagaagg tggagagaga      300
gacagagaca gatccattcg attagtgaac ggatctcgac ggtatcgata ctagtattat      360
gcccagtaca tgaccttatg ggactttcct acttggcagt acatctacgt attagtcatc      420
gctattacca tggtgatgcg gttttggcag tacatcaatg ggcgtggata gcggtttgac      480
tcacggggat ttccaagtct ccacccatt gacgtcaatg ggagtttgtt ttggcaccaa      540
aatcaacggg actttccaaa atgtcgtaac aactccgccc cattgacgca aatgggcggt      600
aggcgtgtac ggtgggaggt ctatataagc agagctcgtt tagtgaaccg tcagatcgcc      660
tggagacgcc atccacgctg ttttgacctc catagaagat tctagaacca tggctagcgt      720
gagcaagggc gaggagctgt tcaccggggt ggtgcccatc ctggtcgagc tggacggcga      780
cgtaaacggc cacaagttca gcgtgtccgg cgagggcgag ggcgatgcca cctacggcaa      840
gctgaccctg aagttcatct gcaccaccgg caagctgccc gtgccctggc ccaccctcgt      900
gaccaccctg acctacggcg tgcagtgctt cagccgctac cccgaccaca tgaagcagca      960
cgacttcttc aagtccgcca tgcccgaagg ctacgtccag gagcgcacca tcttcttcaa     1020
ggacgacggc aactacaaga cccgcgccga ggtgaagttc gagggcgaca ccctggtgaa     1080
ccgcatcgag ctgaagggca tcgacttcaa ggaggacggc aacatcctgg ggcacaagct     1140
ggagtacaac tacaacagcc acaacgtcta tatcatggcc gacaagcaga agaacggcat     1200
caaggtgaac ttcaagatcc gccacaacat cgaggacggc agcgtgcagc tcgccgacca     1260
ctaccagcag aacaccccca tcggcgacgg ccccgtgctg ctgcccgaca accactacct     1320
gagcacccag tccgccctga gcaaagaccc caacgagaag cgcgatcaca tggtcctgct     1380
ggagttcgtg accgccgccg ggatcactct cggcatggac gagctgtaca agtgatccgt     1440
tcaactagca gaccgtttaa acaattcaag ctttttcaa ttctcgacct cgagacaaat     1500
ggcagtattc atccacaatt ttaaaagaaa aggggggatt ggggggtaca gtgcagggga     1560
aagaatagta gacataatag caacagacat acaaactaaa gaattacaaa aacaaattac     1620
aaaaattcaa aattttcggg tttattacag ggacagcaga gatccagttt ggccgcggct     1680 cgaggggggtt ggggttgcgc cttttccaag gcagccctgg gtttgcgcag ggacgcggct     1740
gctctgggcg tggttccggg aaacgcagcg cgccgaccc tgggtctcgc acattcttca     1800
cgtccgttcg cagcgtcacc cggatcttcg ccgctaccct tgtgggcccc ccggcgacgc     1860
ttcctgctcc gccccctaagt cgggaaggtt ccttgcggtt cgcggcgtgc cggacgtgac     1920
aaacggaagc cgcacgtctc actagtaccc tcgcagacgg acagcgccag ggagcaatgg     1980
cagcgcgccg accgcgatgg gctgtggcca atagcggctg ctcagcaggg cgcgccgaga     2040
gcagcggccg ggaaggggcg gtgcgggagg cggggtgtgg ggcggtagtg tgggccctgt     2100
tcctgcccgc gcggtgttcc gcattctgca agcctccgga gcgcacgtcg gcagtcggct     2160
ccctcgttga ccgaatcacc gacctctctc cccagggga tccaccggag cttaccatga     2220
ccgagtacaa gcccacggtg cgcctcgcca ccgcgacga cgtccccagg gcggtacgca     2280
ccctcgccgc cgcgttcgcc gactaccccg ccacgcgcca ccgtcgat ccggaccgcc     2340 acatcgagcg ggtcaccgag ctgcaagaac tcttcctcac gcgcgtcggg ctcgacatcg     2400
gcaaggtgtg ggtcgcggac gacggcgccg cggtggcggt ctggaccacg ccggagagcg     2460
tcgaagcggg ggcggtgttc gccgagatcg gcccgcgcat ggccgagttg agcggttccc     2520
```

-continued

```
ggctggccgc gcagcaacag atggaaggcc tcctggcgcc gcaccggccc aaggagcccg    2580
cgtggttcct ggccaccgtc ggcgtctcgc ccgaccacca gggcaagggt ctgggcagcg    2640
ccgtcgtgct ccccggagtg gaggcggccg agcgcgccgg ggtgcccgcc ttcctggaga    2700
cctccgcgcc ccgcaacctc cccttctacg agcggctcgg cttcaccgtc accgccgacg    2760
tcgaggtgcc cgaaggaccg cgcacctggt gcatgacccg caagcccggt gcctgacgcc    2820
cgccccacga cccgcagcgc ccgaccgaaa ggagcgcacg accccatgca tcgttaagag    2880
ctcggtacct ttaagaccaa tgacttacaa ggcagctgta gatcttagcc acttttaaa    2940 agaaaagggg ggactggaag ggctaattca ctcccaacga agacaagatc tgcttttgc    3000 ttgtactggg tctctctggt tagaccagat ctgagcctgg gagctctctc gctaactagg    3060
gaacccactg cttaagcctc aataaagctt gccttgagtg cttcaagtag tgtgtgcccg    3120
tctgttgtgt gactctggta actagagatc cctcagaccc ttttagtcag tgtggaaaat    3180
ctctagcagt agtagttcat gtcatcttat tattcagtat ttataacttg caaagaaatg    3240
aatatcagag agtgagagga acttgtttat tgcagcttat aatggttaca ataaagcaa    3300 tagcatcaca aatttcacaa ataaagcatt tttttcactg cattctagtt gtggtttgtc    3360
caaactcatc aatgtatctt atcatgtctg gctctagcta tcccgcccct aactccgccc    3420
atcccgcccc taactccgcc cagttccgcc cattctccgc cccatggctg actaattttt    3480
tttatttatg cagagcaaac cgcccagagt agaagatgga ttggggcacg ctgcagacga    3540
tcctgggggg tgtgaacaaa cactccacca gcattggaaa gatctggctc accgtcctct    3600 tcattttcg cattatgatc ctcattgtgg ctgcaaagga ggtgtgggga gatgagcagg    3660
ccgactttgt ctgcaacacc ctgcagccag gctgcaagaa cgtgtgctac gatcactact    3720
tccccatctc ccacatccgg ctatgggccc tgcagctgat cttcgtgtcc acgccagcgc    3780
tcctagtggc catgcacgtg gcctaccgga gacat                              3815
```

<210> SEQ ID NO 9
<211> LENGTH: 39
<212> TYPE: DNA
<213> ORGANISM: Artificial Sequence
<220> FEATURE:
<223> OTHER INFORMATION: CMVpro-r
<220> FEATURE:
<221> NAME/KEY: primer_bind
<222> LOCATION: (1)..(39)

<400> SEQUENCE: 9
gcagtactca tggtggcgag ctcggtacca agcttaagt                           39

<210> SEQ ID NO 10
<211> LENGTH: 39
<212> TYPE: DNA
<213> ORGANISM: Artificial Sequence
<220> FEATURE:
<223> OTHER INFORMATION: cher-f
<220> FEATURE:
<221> NAME/KEY: primer_bind
<222> LOCATION: (1)..(39)

<400> SEQUENCE: 10
agacgacctt ccgccaccat ggtgagcaag ggcgaggag                           39

<210> SEQ ID NO 11
<211> LENGTH: 42
<212> TYPE: DNA

```
<213> ORGANISM: Artificial Sequence
<220> FEATURE:
<223> OTHER INFORMATION: bet-f
<220> FEATURE:
<221> NAME/KEY: primer_bind
<222> LOCATION: (1)..(42)

<400> SEQUENCE: 11
cttggtaccg agctcgccac catgagtact gcactcgcaa cg                42

<210> SEQ ID NO 12
<211> LENGTH: 37
<212> TYPE: DNA
<213> ORGANISM: Artificial Sequence
<220> FEATURE:
<223> OTHER INFORMATION: bet-r
<220> FEATURE:
<221> NAME/KEY: primer_bind
<222> LOCATION: (1)..(37)

<400> SEQUENCE: 12
ccgcggatct cactatcatg ctgccacctt ctgctct                     37

<210> SEQ ID NO 13
<211> LENGTH: 35
<212> TYPE: DNA
<213> ORGANISM: Artificial Sequence
<220> FEATURE:
<223> OTHER INFORMATION: IRES-I-f
<220> FEATURE:
<221> NAME/KEY: primer_bind
<222> LOCATION: (1)..(35)

<400> SEQUENCE: 13
aaggtggcag catgatagtg agatccgcgg ccgca                       35

<210> SEQ ID NO 14
<211> LENGTH: 36
<212> TYPE: DNA
<213> ORGANISM: Artificial Sequence
<220> FEATURE:
<223> OTHER INFORMATION: IRES-I-r
<220> FEATURE:
<221> NAME/KEY: primer_bind
<222> LOCATION: (1)..(36)

<400> SEQUENCE: 14
cggtgtcatg gtggcggaag gtcgtctcct tgtggg                      36

<210> SEQ ID NO 15
<211> LENGTH: 40
<212> TYPE: DNA
<213> ORGANISM: Artificial Sequence
<220> FEATURE:
<223> OTHER INFORMATION: exo-f
<220> FEATURE:
<221> NAME/KEY: primer_bind
<222> LOCATION: (1)..(40)

<400> SEQUENCE: 15
agacgacctt ccgccaccat gacaccggac attatcctgc                  40

<210> SEQ ID NO 16
<211> LENGTH: 38
<212> TYPE: DNA
<213> ORGANISM: Artificial Sequence
<220> FEATURE:
<223> OTHER INFORMATION: exo-r
<220> FEATURE:
```

```
<221> NAME/KEY: primer_bind
<222> LOCATION: (1)..(38)

<400> SEQUENCE: 16
gccgcggatc tctagatcat cgccattgct ccccaaat                            38

<210> SEQ ID NO 17
<211> LENGTH: 35
<212> TYPE: DNA
<213> ORGANISM: Artificial Sequence
<220> FEATURE:
<223> OTHER INFORMATION: IRES-II-f
<220> FEATURE:
<221> NAME/KEY: primer_bind
<222> LOCATION: (1)..(35)

<400> SEQUENCE: 17
gagcaatggc gatgatctag agatccgcgg ccgca                               35

<210> SEQ ID NO 18
<211> LENGTH: 40
<212> TYPE: DNA
<213> ORGANISM: Artificial Sequence
<220> FEATURE:
<223> OTHER INFORMATION: IRES-II-r
<220> FEATURE:
<221> NAME/KEY: primer_bind
<222> LOCATION: (1)..(40)

<400> SEQUENCE: 18
ccttgctcac catggtggcg gaaggtcgtc tccttgtggg                          40

<210> SEQ ID NO 19
<211> LENGTH: 22
<212> TYPE: DNA
<213> ORGANISM: Artificial Sequence
<220> FEATURE:
<223> OTHER INFORMATION: EB-VEC-f
<220> FEATURE:
<221> NAME/KEY: primer_bind
<222> LOCATION: (1)..(22)

<400> SEQUENCE: 19
acgcctgggg taatgactct ct                                             22

<210> SEQ ID NO 20
<211> LENGTH: 21
<212> TYPE: DNA
<213> ORGANISM: Artificial Sequence
<220> FEATURE:
<223> OTHER INFORMATION: EB-VEC-r
<220> FEATURE:
<221> NAME/KEY: primer_bind
<222> LOCATION: (1)..(21)

<400> SEQUENCE: 20
ctcgaggtga agacgaaagg g                                              21

<210> SEQ ID NO 21
<211> LENGTH: 47
<212> TYPE: DNA
<213> ORGANISM: Artificial Sequence
<220> FEATURE:
<223> OTHER INFORMATION: L122-VEC-f
<220> FEATURE:
<221> NAME/KEY: primer_bind
<222> LOCATION: (1)..(47)

<400> SEQUENCE: 21
``` cccttcgtc ttcacctcga ggtaagttag gcagggatat tcaccat 47

<210> SEQ ID NO 22
<211> LENGTH: 25
<212> TYPE: DNA
<213> ORGANISM: Artificial Sequence
<220> FEATURE:
<223> OTHER INFORMATION: L122-U-r
<220> FEATURE:
<221> NAME/KEY: primer_bind
<222> LOCATION: (1)..(25)

<400> SEQUENCE: 22
tccctagtta gcgagagagc tccca 25

<210> SEQ ID NO 23
<211> LENGTH: 25
<212> TYPE: DNA
<213> ORGANISM: Artificial Sequence
<220> FEATURE:
<223> OTHER INFORMATION: L122-D-f
<220> FEATURE:
<221> NAME/KEY: primer_bind
<222> LOCATION: (1)..(25)

<400> SEQUENCE: 23
gggagctctc tcgctaacta gggaa 25

<210> SEQ ID NO 24
<211> LENGTH: 49
<212> TYPE: DNA
<213> ORGANISM: Artificial Sequence
<220> FEATURE:
<223> OTHER INFORMATION: L122-VEC-r
<220> FEATURE:
<221> NAME/KEY: primer_bind
<222> LOCATION: (1)..(49)

<400> SEQUENCE: 24
agagagtcat taccccaggc gtctgcataa ataaaaaaaa ttagtcagc 49

<210> SEQ ID NO 25
<211> LENGTH: 19
<212> TYPE: DNA
<213> ORGANISM: Artificial Sequence
<220> FEATURE:
<223> OTHER INFORMATION: GJB-EX1-f
<220> FEATURE:
<221> NAME/KEY: primer_bind
<222> LOCATION: (1)..(19)

<400> SEQUENCE: 25
ggggtgcggt taaaaggcg 19

<210> SEQ ID NO 26
<211> LENGTH: 40
<212> TYPE: DNA
<213> ORGANISM: Artificial Sequence
<220> FEATURE:
<223> OTHER INFORMATION: GJB-EX1-FU-r
<220> FEATURE:
<221> NAME/KEY: primer_bind
<222> LOCATION: (1)..(40)

<400> SEQUENCE: 26
gtgaatatcc ctgcctaact tacctgcgtc gggaggaagc 40

```
<210> SEQ ID NO 27
<211> LENGTH: 9177
<212> TYPE: DNA
<213> ORGANISM: Artificial Sequence
<220> FEATURE:
<223> OTHER INFORMATION: pCRISPR/Cas9n(D10A)L

<400> SEQUENCE: 27
```

| | | | | | |
|---|---|---|---|---|---|
| gagggcctat | ttcccatgat | tccttcatat | ttgcatatac | gatacaaggc | tgttagagag | 60 |
| ataattggaa | ttaatttgac | tgtaaacaca | aagatattag | tacaaaatac | gtgacgtaga | 120 |
| aagtaataat | ttcttgggta | gtttgcagtt | ttaaaattat | gttttaaaat | ggactatcat | 180 |
| atgcttaccg | taacttgaaa | gtatttcgat | ttcttggctt | tatatatctt | gtggaaagga | 240 |
| cgaaacaccg | cccaatccat | cttctactcg | ttttagagct | agaaatagca | agttaaaata | 300 |
| aggctagtcc | gttatcaact | tgaaaaagtg | gcaccgagtc | ggtgcttttt | tgttttagag | 360 |
| ctagaaatag | caagttaaaa | taaggctagt | ccgtttttag | cgcgtgcgcc | aattctgcag | 420 |
| acaaatggct | ctagaggtac | ccgttacata | acttacggta | aatggcccgc | ctggctgacc | 480 |
| gcccaacgac | ccccgcccat | tgacgtcaat | agtaacgcca | atagggactt | tccattgacg | 540 |
| tcaatgggtg | gagtatttac | ggtaaactgc | ccacttggca | gtacatcaag | tgtatcatat | 600 |
| gccaagtacg | cccccctattg | acgtcaatga | cggtaaatgg | cccgcctggc | attgtgccca | 660 |
| gtacatgacc | ttatgggact | ttcctacttg | gcagtacatc | tacgtattag | tcatcgctat | 720 |
| taccatggtc | gaggtgagcc | ccacgttctg | cttcactctc | cccatctccc | cccctcccc | 780 |
| accccaatt | ttgtatttat | ttattttta | attattttgt | gcagcgatgg | gggcggggg | 840 |
| gggggggggg | cgcgcgccag | gcggggcggg | gcggggcgag | gggcggggcg | gggcgaggcg | 900 |
| gagaggtgcg | gcggcagcca | atcagagcgg | cgcgctccga | aagtttcctt | ttatggcgag | 960 |
| gcggcggcgg | cggcggccct | ataaaaagcg | aagcgcgcgg | cgggcgggag | tcgctgcgac | 1020 |
| gctgccttcg | ccccgtgccc | cgctccgccg | ccgcctcgcg | ccgcccgccc | cggctctgac | 1080 |
| tgaccgcgtt | actcccacag | gtgagcgggc | gggacggccc | ttctcctccg | ggctgtaatt | 1140 |
| agctgagcaa | gaggtaaggg | tttaaggat | ggttggttgg | tggggtatta | atgtttaatt | 1200 |
| acctggagca | cctgcctgaa | atcacttttt | ttcaggttgg | accggtgcca | ccatggacta | 1260 |
| taaggaccac | gacggagact | acaaggatca | tgatattgat | tacaaagacg | atgacgataa | 1320 |
| gatgccccca | aagaagaagc | ggaaggtcgg | tatccacgga | gtcccagcag | ccgacaagaa | 1380 |
| gtacagcatc | ggcctggcca | tcggcaccaa | ctctgtgggc | tgggccgtga | tcaccgacga | 1440 |
| gtacaaggtg | cccagcaaga | aattcaaggt | gctgggcaac | accgaccggc | acagcatcaa | 1500 |
| gaagaacctg | atcggagccc | tgctgttcga | cagcggcgaa | acagccgagg | ccacccggct | 1560 |
| gaagagaacc | gccagaagaa | gatacaccag | acgaagaac | cggatctgct | atctgcaaga | 1620 |
| gatcttcagc | aacgagatgg | ccaaggtgga | cgacagcttc | ttccacagac | tggaagagtc | 1680 |
| cttcctggtg | gaagaggata | agaagcacga | gcggcacccc | atcttcggca | acatcgtgga | 1740 |
| cgaggtggcc | taccacgaga | gtaccccac | catctaccac | ctgagaaaga | aactggtgga | 1800 |
| cagcaccgac | aaggccgacc | tgcggctgat | ctatctggcc | ctggcccaca | tgatcaagtt | 1860 |
| ccggggccac | ttcctgatcg | agggcgacct | gaaccccgac | aacagcgacg | tggacaagct | 1920 |
| gttcatccag | ctggtgcaga | cctacaacca | gctgttcgag | gaaaacccca | tcaacgccag | 1980 |
| cggcgtggac | gccaaggcca | tcctgtctgc | cagactgagc | aagagcagac | ggctggaaaa | 2040 |
| tctgatcgcc | cagctgcccg | gcgagaagaa | gaatggcctg | ttcggcaacc | tgattgccct | 2100 |

```
gagcctgggc ctgaccccca acttcaagag caacttcgac ctggccgagg atgccaaact   2160
gcagctgagc aaggacacct acgacgacga cctggacaac ctgctggccc agatcggcga   2220
ccagtacgcc gacctgtttc tggccgccaa gaacctgtcc gacgccatcc tgctgagcga   2280
catcctgaga gtgaacaccg agatcaccaa ggccccctg agcgcctcta tgatcaagag    2340
atacgacgag caccaccagg acctgaccct gctgaaagct ctcgtgcggc agcagctgcc   2400
tgagaagtac aaagagattt tcttcgacca gagcaagaac ggctacgccg gctacattga   2460
cggcggagcc agccaggaag agttctacaa gttcatcaag cccatcctgg aaaagatgga   2520
cggcaccgag gaactgctcg tgaagctgaa cagagaggac ctgctgcgga agcagcggac   2580
cttcgacaac ggcagcatcc cccaccagat ccacctggga gagctgcacg ccattctgcg   2640
gcggcaggaa gatttttacc cattcctgaa ggacaaccgg aaaagatcg agaagatcct    2700
gaccttccgc atcccctact acgtgggccc tctggccagg ggaaacagca gattcgcctg   2760
gatgaccaga aagagcgagg aaaccatcac cccctggaac ttcgaggaag tggtggacaa   2820
gggcgcttcc gcccagagct tcatcgagcg gatgaccaac ttcgataaga acctgcccaa   2880
cgagaaggtg ctgcccaagc acagcctgct gtacgagtac ttcaccgtgt ataacgagct   2940
gaccaaagtg aaatacgtga ccgagggaat gagaaagccc gccttcctga gcggcgagca   3000
gaaaaaggcc atcgtggacc tgctgttcaa gaccaaccgg aaagtgaccg tgaagcagct   3060
gaaagaggac tacttcaaga aaatcgagtg cttcgactcc gtggaaatct ccggcgtgga   3120
agatcggttc aacgcctccc tgggcacata ccacgatctg ctgaaaatta tcaaggacaa   3180
ggacttcctg gacaatgagg aaaacgagga cattctggaa gatatcgtgc tgaccctgac   3240
actgtttgag acagagagag tgatcgagga acggctgaaa acctatgccc acctgttcga   3300
cgacaaagtg atgaagcagc tgaagcggcg gagatatacc ggctggggca ggctgagccg   3360
gaagctgatc aacggcatcc gggacaagca gtccggcaag acaatcctgg atttcctgaa   3420
gtccgacggc ttcgccaaca gaaacttcat gcagctgatc cacgacgaca gcctgacctt   3480
taaagaggac atccagaaag cccaggtgtc cggccagggc gatagcctgc acgagcacat   3540
tgccaatctg gccggcagcc ccgccattaa gaagggcatc ctgcagacag tgaaggtggt   3600
ggacgagctc gtgaaagtga tgggccggca caagcccgag aacatcgtga tcgaaatggc   3660
cagagagaac cagaccaccc agaagggaca gaagaacagc cgcgagagaa tgaagcggat   3720
cgaagagggc atcaaagagc tgggcagcca gatcctgaaa gaacacccg tggaaaacac    3780
ccagctgcag aacgagaagc tgtacctgta ctacctgcag aatgggcggg atatgtacgt   3840
ggaccaggaa ctggacatca accggctgtc cgactacgat gtggaccata tcgtgcctca   3900
gagctttctg aaggacgact ccatcgacaa caaggtgctg accagaagcg acaagaaccg   3960
gggcaagagc gacaacgtgc cctccgaaga ggtcgtgaag aagatgaaga actactggcg   4020
gcagctgctg aacgccaagc tgattaccca gagaaagttc gacaatctga ccaaggccga   4080
gagaggcggc ctgagcgaac tggataaggc cggcttcatc aagagacagc tggtggaaac   4140
ccggcagatc acaaagcacg tggcacagat cctggactcc cggatgaaca ctaagtacga   4200
cgagaatgac aagctgatcc gggaagtgaa agtgatcacc ctgaagtcca gctggtgtc    4260
cgatttccgg aaggatttcc agttttacaa agtgcgcgag atcaacaact accaccacgc   4320
ccacgacgcc tacctgaacg ccgtcgtggg aaccgccctg atcaaaaagt accctaagct   4380
ggaaagcgag ttcgtgtacg gcgactacaa ggtgtacgac gtgcgaaaga tgatcgccaa   4440
gagcgagcag gaaatcggca aggctaccgc caagtacttc ttctacagca acatcatgaa   4500
```

-continued

| | | | | | |
|---|---|---|---|---|---|
| cttttttcaag | accgagatta | ccctggccaa | cggcgagatc | cggaagcggc | tctctgatcga | 4560 |
| gacaaacggc | gaaaccgggg | agatcgtgtg | ggataagggc | cgggattttg | ccaccgtgcg | 4620 |
| gaaagtgctg | agcatgcccc | aagtgaatat | cgtgaaaaag | accgaggtgc | agacaggcgg | 4680 |
| cttcagcaaa | gagtctatcc | tgcccaagag | gaacagcgat | aagctgatcg | ccagaaagaa | 4740 |
| ggactgggac | cctaagaagt | acggcggctt | cgacagcccc | accgtggcct | attctgtgct | 4800 |
| ggtggtggcc | aaagtggaaa | agggcaagtc | caagaaactg | aagagtgtga | aagagctgct | 4860 |
| ggggatcacc | atcatggaaa | gaagcagctt | cgagaagaat | cccatcgact | tctggaagc | 4920 |
| caagggctac | aaagaagtga | aaaggacct | gatcatcaag | ctgcctaagt | actccctgtt | 4980 |
| cgagctggaa | aacggccgga | agagaatgct | ggcctctgcc | ggcgaactgc | agaagggaaa | 5040 |
| cgaactggcc | ctgccctcca | aatatgtgaa | cttcctgtac | ctggccagcc | actatgagaa | 5100 |
| gctgaagggc | tcccccgagg | ataatgagca | gaaacagctg | tttgtggaac | agcacaagca | 5160 |
| ctacctggac | gagatcatcg | agcagatcag | cgagttctcc | aagagagtga | tcctggccga | 5220 |
| cgctaatctg | gacaaagtgc | tgtccgccta | caacaagcac | cgggataagc | ccatcagaga | 5280 |
| gcaggccgag | aatatcatcc | acctgtttac | cctgaccaat | ctgggagccc | ctgccgcctt | 5340 |
| caagtacttt | gacaccacca | tcgaccggaa | gaggtacacc | agcaccaaag | aggtgctgga | 5400 |
| cgccaccctg | atccaccaga | gcatcaccgg | cctgtacgag | acacgatcg | acctgtctca | 5460 |
| gctgggaggc | gacaaaggc | cggcggccac | gaaaaaggcc | ggccaggcaa | aaagaaaaa | 5520 |
| ggaattcggc | agtggagagg | gcagaggaag | tctgctaaca | tgcggtgacg | tcgaggagaa | 5580 |
| tcctggccca | atgaccgagt | acaagcccac | ggtgcgcctc | gccacccgcg | acgacgtccc | 5640 |
| cagggccgta | cgcaccctcg | ccgccgcgtt | cgccgactac | cccgccacgc | gccacaccgt | 5700 |
| cgatccggac | cgccacatcg | agcgggtcac | cgagctgcaa | gaactcttcc | tcacgcgcgt | 5760 |
| cgggctcgac | atcggcaagg | tgtgggtcgc | ggacgacggc | gccgcggtgg | cggtctggac | 5820 |
| cacgccggag | agcgtcgaag | cggggcggt | gttcgccgag | atcggcccgc | gcatggccga | 5880 |
| gttgagcggt | tcccggctgg | ccgcgcagca | acagatggaa | ggcctcctgg | cgccgcaccg | 5940 |
| gcccaaggag | cccgcgtggt | tcctggccac | cgtcggcgtc | tcgcccgacc | accagggcaa | 6000 |
| gggtctgggc | agcgccgtcg | tgctccccgg | agtggaggcg | gccgagcgcg | ccggggtgcc | 6060 |
| cgccttcctg | gagacctccg | cgccccacaa | cctccccttc | tacgagcggc | tcggcttcac | 6120 |
| cgtcaccgcc | gacgtcgagg | tgcccgaagg | accgcgcacc | tggtgcatga | cccgcaagcc | 6180 |
| cggtgcctga | gaattctaac | tagagctcgc | tgatcagcct | cgactgtgcc | ttctagttgc | 6240 |
| cagccatctg | ttgtttgccc | ctcccccgtg | ccttccttga | ccctggaagg | tgccactccc | 6300 |
| actgtccttt | cctaataaaa | tgaggaaatt | gcatcgcatt | gtctgagtag | gtgtcattct | 6360 |
| attctggggg | gtggggtggg | gcaggacagc | aagggggagg | attgggaaga | gaatagcagg | 6420 |
| catgctgggg | agcggccgca | ggaaccccta | gtgatggagt | tggccactcc | ctctctgcgc | 6480 |
| gctcgctcgc | tcactgaggc | cgggcgacca | aaggtcgccc | gacgcccggg | ctttgcccgg | 6540 |
| gcggcctcag | tgagcgagcg | agcgcgcagc | tgcctgcagg | ggcgcctgat | gcggtatttt | 6600 |
| ctccttacgc | atctgtgcgg | tatttcacac | cgcatacgtc | aaagcaacca | tagtacgcgc | 6660 |
| cctgtagcgg | cgcattaagc | gcggcgggtg | tggtggttac | gcgcagcgtg | accgctacac | 6720 |
| ttgccagcgc | cctagcgccc | gctcctttcg | ctttcttccc | ttcctttctc | gccacgttcg | 6780 |
| ccggctttcc | ccgtcaagct | ctaaatcggg | ggctcccttt | agggttccga | tttagtgctt | 6840 |

-continued

```
tacggcacct cgaccccaaa aaacttgatt tgggtgatgg ttcacgtagt gggccatcgc    6900
cctgatagac ggttttttcgc cctttgacgt tggagtccac gttctttaat agtggactct   6960
tgttccaaac tggaacaaca ctcaaccccta tctcgggcta ttcttttgat ttataaggga   7020
ttttgccgat ttcggcctat tggttaaaaa atgagctgat ttaacaaaaa tttaacgcga   7080
attttaacaa atattaacg tttacaattt tatggtgcac tctcagtaca atctgctctg    7140
atgccgcata gttaagccag ccccgacacc cgccaacacc cgctgacgcg ccctgacggg   7200
cttgtctgct cccggcatcc gcttacagac aagctgtgac cgtctccggg agctgcatgt   7260
gtcagaggtt ttcaccgtca tcaccgaaac gcgcgagacg aaagggcctc gtgatacgcc   7320
tatttttata ggttaatgtc atgataataa tggtttctta dacgtcaggt ggcacttttc   7380
ggggaaatgt gcgcggaacc cctatttgtt tattttttcta aatacattca aatatgtatc   7440
cgctcatgag acaataaccc tgataaatgc ttcaataata ttgaaaaagg aagagtatga   7500
gtattcaaca tttccgtgtc gcccttattc ccttttttgc ggcattttgc cttcctgttt   7560
ttgctcaccc agaaacgctg gtgaaagtaa aagatgctga agatcagttg ggtgcacgag   7620
tgggttacat cgaactggat ctcaacagcg gtaagatcct tgagagtttt cgccccgaag   7680
aacgttttcc aatgatgagc acttttaaag ttctgctatg tggcgcggta ttatcccgta   7740
ttgacgccgg gcaagagcaa ctcggtcgcc gcatacacta ttctcagaat gacttggttg   7800
agtactcacc agtcacagaa aagcatctta cggatggcat gacagtaaga gaattatgca   7860
gtgctgccat aaccatgagt gataacactg cggccaactt acttctgaca acgatcggag   7920
gaccgaagga gctaaccgct tttttgcaca acatggggga tcatgtaact cgccttgatc   7980
gttgggaacc ggagctgaat gaagccatac caaacgacga gcgtgacacc acgatgcctg   8040
tagcaatggc aacaacgttg cgcaaactat taactggcga actacttact ctagcttccc   8100
ggcaacaatt aatagactgg atggaggcgg ataaagttgc aggaccactt ctgcgctcgg   8160
cccttccggc tggctggttt attgctgata aatctggagc cggtgagcgt ggaagccgcg   8220
gtatcattgc agcactgggg ccagatggta agccctcccg tatcgtagtt atctacacga   8280
cggggagtca ggcaactatg gatgaacgaa atagacagat cgctgagata ggtgcctcac   8340
tgattaagca ttggtaactg tcagaccaag tttactcata tatactttag attgatttaa   8400
aacttcattt ttaatttaaa aggatctagg tgaagatcct ttttgataat ctcatgacca   8460
aaatccctta acgtgagttt tcgttccact gagcgtcaga ccccgtagaa aagatcaaag   8520
gatcttcttg agatcctttt tttctgcgcg taatctgctg cttgcaaaca aaaaaaccac   8580
cgctaccagc ggtggtttgt ttgccggatc aagagctacc aactcttttt ccgaaggtaa   8640
ctggcttcag cagagcgcag ataccaaata ctgtccttct agtgtagccg tagttaggcc   8700
accacttcaa gaactctgta gcaccgccta catacctcgc tctgctaatc ctgttaccag   8760
tggctgctgc cagtggcgat aagtcgtgtc ttaccgggtt ggactcaaga cgatagttac   8820
cggataaggc gcagcggtcg ggctgaacgg ggggttcgtg cacacagccc agcttggagc   8880
gaacgaccta caccgaactg agatacctac agcgtgagct atgagaaagc gccacgcttc   8940
ccgaagggag aaaggcggac aggtatccgg taagcggcag ggtcggaaca ggagagcgca   9000
cgagggagct tccaggggga aacgcctggt atctttatag tcctgtcggg tttcgccacc   9060
tctgacttga gcgtcgattt ttgtgatgct cgtcaggggg gcggagccta tggaaaaacg   9120
ccagcaacgc ggcctttttta cggttcctgg ccttttgctg ccttttgct cacatgt     9177
```

<210> SEQ ID NO 28
<211> LENGTH: 8508
<212> TYPE: DNA
<213> ORGANISM: Artificial Sequence
<220> FEATURE:
<223> OTHER INFORMATION: pCRISPR/Cas9n(D10A)R

<400> SEQUENCE: 28

| | | | | | | |
|---|---|---|---|---|---|---|
| gagggcctat | ttcccatgat | tccttcatat | ttgcatatac | gatacaaggc | tgttagagag | 60 |
| ataattggaa | ttaatttgac | tgtaaacaca | aagatattag | tacaaaatac | gtgacgtaga | 120 |
| aagtaataat | ttcttgggta | gtttgcagtt | ttaaaattat | gttttaaaat | ggactatcat | 180 |
| atgcttaccg | taacttgaaa | gtatttcgat | ttcttggctt | tatatatctt | gtggaaagga | 240 |
| cgaaacaccg | acaaacactc | caccagcatg | ttttagagct | agaaatagca | agttaaaata | 300 |
| aggctagtcc | gttatcaact | tgaaaaagtg | gcaccgagtc | ggtgcttttt | tgttttagag | 360 |
| ctagaaatag | caagttaaaa | taaggctagt | ccgttttag | cgcgtgcgcc | aattctgcag | 420 |
| acaaatggct | ctagaggtac | ccgttacata | acttacggta | aatggcccgc | ctggctgacc | 480 |
| gcccaacgac | ccccgcccat | tgacgtcaat | agtaacgcca | atagggactt | tccattgacg | 540 |
| tcaatgggtg | gagtatttac | ggtaaactgc | ccacttggca | gtacatcaag | tgtatcatat | 600 |
| gccaagtacg | cccccctattg | acgtcaatga | cggtaaatgg | cccgcctggc | attgtgccca | 660 |
| gtacatgacc | ttatgggact | ttcctacttg | gcagtacatc | tacgtattag | tcatcgctat | 720 |
| taccatggtc | gaggtgagcc | ccacgttctg | cttcactctc | cccatctccc | cccctcccc | 780 |
| accccaatt | ttgtatttat | ttattttta | attatttgt | gcagcgatgg | gggcgggggg | 840 |
| gggggggggg | cgcgcgccag | gcggggcggg | gcggggcgag | gggcggggcg | gggcgaggcg | 900 |
| gagaggtgcg | gcggcagcca | atcagagcgg | cgcgctccga | aagtttcctt | ttatggcgag | 960 |
| gcggcggcgg | cggcggccct | ataaaaagcg | aagcgcgcgg | cgggcgggag | tcgctgcgac | 1020 |
| gctgccttcg | ccccgtgccc | cgctccgccg | ccgcctcgcg | ccgcccgccc | cggctctgac | 1080 |
| tgaccgcgtt | actcccacag | gtgagcgggc | gggacggccc | ttctcctccg | ggctgtaatt | 1140 |
| agctgagcaa | gaggtaaggg | tttaaggat | ggttggttgg | tggggtatta | atgtttaatt | 1200 |
| acctggagca | cctgcctgaa | atcacttttt | ttcaggttgg | accggtgcca | ccatggacta | 1260 |
| taaggaccac | gacggagact | acaaggatca | tgatattgat | tacaaagacg | atgacgataa | 1320 |
| gatgccccca | aagaagaagc | ggaaggtcgg | tatccacgga | gtcccagcag | ccgacaagaa | 1380 |
| gtacagcatc | ggcctggcca | tcggcaccaa | ctctgtgggc | tgggccgtga | tcaccgacga | 1440 |
| gtacaaggtg | cccagcaaga | aattcaaggt | gctgggcaac | accgaccggc | acagcatcaa | 1500 |
| gaagaacctg | atcggagccc | tgctgttcga | cagcggcgaa | acagccgagg | ccacccggct | 1560 |
| gaagagaacc | gccagaagaa | gatacaccag | acgaagaac | cggatctgct | atctgcaaga | 1620 |
| gatcttcagc | aacgagatgg | ccaaggtgga | cgacagcttc | ttccacagac | tggaagagtc | 1680 |
| cttcctggtg | gaagaggata | agaagcacga | gcggcacccc | atcttcggca | acatcgtgga | 1740 |
| cgaggtggcc | taccacgaga | agtaccccac | catctaccac | ctgagaaaga | aactggtgga | 1800 |
| cagcaccgac | aaggccgacc | tgcggctgat | ctatctggcc | ctggcccaca | tgatcaagtt | 1860 |
| ccggggccac | ttcctgatcg | agggcgacct | gaaccccgac | aacagcgacg | tggacaagct | 1920 |
| gttcatccag | ctggtgcaga | cctacaacca | gctgttcgag | gaaaacccca | tcaacgccag | 1980 |
| cggcgtggac | gccaaggcca | tcctgtctgc | cagactgagc | aagagcagac | ggctggaaaa | 2040 |
| tctgatcgcc | cagctgcccg | gcgagaagaa | gaatggcctg | ttcggcaacc | tgattgccct | 2100 |

-continued

```
gagcctgggc ctgacccca acttcaagag caacttcgac ctggccgagg atgccaaact      2160
gcagctgagc aaggacacct acgacgacga cctggacaac ctgctggccc agatcggcga      2220
ccagtacgcc gacctgtttc tggccgccaa gaacctgtcc gacgccatcc tgctgagcga      2280
catcctgaga gtgaacaccg agatcaccaa ggccccctg agcgcctcta tgatcaagag       2340
atacgacgag caccaccagg acctgaccct gctgaaagct ctcgtgcggc agcagctgcc      2400
tgagaagtac aaagagattt tcttcgacca gagcaagaac ggctacgccg gctacattga      2460
cggcggagcc agccaggaag agttctacaa gttcatcaag cccatcctgg aaaagatgga      2520
cggcaccgag gaactgctcg tgaagctgaa cagagaggac ctgctgcgga agcagcggac      2580
cttcgacaac ggcagcatcc cccaccagat ccacctggga gagctgcacg ccattctgcg      2640
gcggcaggaa gattttacc cattcctgaa ggacaaccgg aaaagatcg agaagatcct       2700 gaccttccgc atccctact acgtgggccc tctggccagg ggaaacagca gattcgcctg      2760
gatgaccaga aagagcgagg aaaccatcac cccctggaac ttcgaggaag tggtggacaa     2820
gggcgcttcc gcccagagct tcatcgagcg gatgaccaac ttcgataaga acctgcccaa     2880
cgagaaggtg ctgcccaagc acagcctgct gtacgagtac ttcaccgtgt ataacgagct     2940
gaccaaagtg aaatacgtga ccgagggaat gagaaagccc gccttcctga gcggcgagca     3000
gaaaaaggcc atcgtggacc tgctgttcaa gaccaaccgg aaagtgaccg tgaagcagct     3060
gaaagaggac tacttcaaga aaatcgagtg cttcgactcc gtggaaatct ccggcgtgga     3120
agatcggttc aacgcctccc tgggcacata ccacgatctg ctgaaaatta tcaaggacaa     3180
ggacttcctg gacaatgagg aaaacgagga cattctggaa gatatcgtgc tgaccctgac     3240 actgttgag gacagagaga tgatcgagga acggctgaaa acctatgccc acctgttcga     3300
cgacaaagtg atgaagcagc tgaagcggcg gagatacacc ggctggggca ggctgagccg     3360
gaagctgatc aacggcatcc gggacaagca gtccggcaag acaatcctgg atttcctgaa     3420
gtccgacggc ttcgccaaca gaaacttcat gcagctgatc cacgacgaca gcctgacctt     3480
taaagaggac atccagaaag cccaggtgtc cggccagggc gatagcctgc acgagcacat     3540
tgccaatctg gccggcagcc ccgccattaa gaagggcatc ctgcagacag tgaaggtggt     3600
ggacgagctc gtgaaagtga tgggccggca caagcccgag aacatcgtga tcgaaatggc     3660
cagagagaac cagaccaccc agaagggaca gaagaacagc cgcgagagaa tgaagcggat     3720
cgaagagggc atcaaagagc tgggcagcca gatcctgaaa gaacaccccg tggaaaacac     3780
ccagctgcag aacgagaagc tgtacctgta ctacctgcag aatgggcggg atatgtacgt     3840
ggaccaggaa ctggacatca accggctgtc cgactacgat gtggaccata tcgtgcctca     3900
gagctttctg aaggacgact ccatcgacaa caaggtgctg accagaagcg acaagaaccg     3960
gggcaagagc gacaacgtgc cctccgaaga ggtcgtgaag aagatgaaga actactggcg     4020
gcagctgctg aacgccaagc tgattaccca gagaaagttc gacaatctga ccaaggccga     4080
gagaggcggc ctgagcgaac tggataaggc cggcttcatc aagagacagc tggtggaaac     4140
ccggcagatc acaaagcacg tggcacagat cctggactcc cggatgaaca ctaagtacga     4200
cgagaatgac aagctgatcc gggaagtgaa agtgatcacc ctgaagtcca gctggtgtc    4260 cgatttccgg aaggatttcc agttttacaa agtgcgcgag atcaacaact accaccacgc     4320
ccacgacgcc tacctgaacg ccgtcgtggg aaccgccctg atcaaaaagt accctaagct     4380
ggaaagcgag ttcgtgtacg cgactacaa ggtgtacgac gtgcgaaga tgatcgccaa      4440 gagcgagcag gaaatcggca aggctaccgc caagtacttc ttctacagca acatcatgaa     4500
```

```
cttttttcaag accgagatta ccctggccaa cggcgagatc cggaagcggc ctctgatcga   4560
gacaaacggc gaaaccgggg agatcgtgtg ggataagggc cgggattttg ccaccgtgcg   4620
gaaagtgctg agcatgcccc aagtgaatat cgtgaaaaag accgaggtgc agacaggcgg   4680
cttcagcaaa gagtctatcc tgcccaagag gaacagcgat aagctgatcg ccagaaagaa   4740
ggactgggac cctaagaagt acggcggctt cgacagcccc accgtggcct attctgtgct   4800
ggtggtggcc aaagtggaaa agggcaagtc caagaaactg aagagtgtga agagctgct   4860
ggggatcacc atcatggaaa gaagcagctt cgagaagaat cccatcgact ttctggaagc   4920
caagggctac aaagaagtga aaaggacct gatcatcaag ctgcctaagt actccctgtt   4980
cgagctggaa acggccgga agagaatgct ggcctctgcc ggcgaactgc agaagggaaa   5040
cgaactggcc ctgccctcca atatgtgaa cttcctgtac ctggccagcc actatgagaa   5100
gctgaagggc tcccccgagg ataatgagca gaaacagctg tttgtggaac agcacaagca   5160
ctacctggac gagatcatcg agcagatcag cgagttctcc aagagagtga tcctggccga   5220
cgctaatctg gacaaagtgc tgtccgccta caacaagcac cgggataagc ccatcagaga   5280
gcaggccgag aatatcatcc acctgtttac cctgaccaat ctgggagccc ctgccgcctt   5340
caagtacttt gacaccacca tcgaccggaa gaggtacacc agcaccaaag aggtgctgga   5400
cgccaccctg atccaccaga gcatcaccgg cctgtacgag acacggatcg acctgtctca   5460
gctgggaggc gacaaaaggc cggcggccac gaaaaaggcc ggccaggcaa aaagaaaaa   5520
ggaattctaa ctagagctcg ctgatcagcc tcgactgtgc cttctagttg ccagccatct   5580
gttgtttgcc cctcccccgt gccttccttg accctggaag gtgccactcc cactgtcctt   5640
tcctaataaa atgaggaaat tgcatcgcat tgtctgagta ggtgtcattc tattctgggg   5700
ggtggggtgg ggcaggacag caaggggggag gattgggaag agaatagcag gcatgctggg   5760
gagcggccgc aggaacccct agtgatggag ttggccactc cctctctgcg cgctcgctcg   5820
ctcactgagg ccgggcgacc aaaggtcgcc cgacgcccgg gctttgcccg gcggcctca   5880
gtgagcgagc gagcgcgcag ctgcctgcag gggcgcctga tgcggtattt tctccttacg   5940
catctgtgcg gtatttcaca ccgcatacgt caaagcaacc atagtacgcg ccctgtagcg   6000
gcgcattaag cgcggcgggt gtggtggtta cgcgcagcgt gaccgctaca cttgccagcg   6060
ccctagcgcc cgctcctttc gctttcttcc cttcctttct cgccacgttc gccggctttc   6120
cccgtcaagc tctaaatcgg gggctccctt tagggttccg atttagtgct ttacggcacc   6180
tcgaccccaa aaaacttgat ttgggtgatg gttcacgtag tgggccatcg ccctgataga   6240
cggtttttcg ccctttgacg ttggagtcca cgttctttaa tagtggactc ttgttccaaa   6300
ctggaacaac actcaaccct atctcgggct attcttttga tttataaggg attttgccga   6360
tttcggccta ttggttaaaa aatgagctga tttaacaaaa atttaacgcg aattttaaca   6420
aaatattaac gttacaatt ttatggtgca ctctcagtac aatctgctct gatgccgcat   6480
agttaagcca gccccgacac ccgccaacac ccgctgacgc gccctgacgg gcttgtctgc   6540
tcccggcatc cgcttacaga caagctgtga ccgtctccgg gagctgcatg tgtcagaggt   6600
tttcaccgtc atcaccgaaa cgcgcgagac gaaagggcct cgtgatacgc ctatttttat   6660
aggttaatgt catgataata atggtttctt agacgtcagg tggcacttt cggggaaatg   6720
tgcgcggaac ccctatttgt ttatttttct aaatacattc aaatatgtat ccgctcatga   6780
gacaataacc ctgataaatg cttcaataat attgaaaaag gaagagtatg agtattcaac   6840
```

-continued

```
atttccgtgt cgcccttatt cccttttttg cggcattttg ccttcctgtt tttgctcacc    6900
cagaaacgct ggtgaaagta aaagatgctg aagatcagtt gggtgcacga gtgggttaca    6960
tcgaactgga tctcaacagc ggtaagatcc ttgagagttt cgccccgaa gaacgttttc     7020
caatgatgag cacttttaaa gttctgctat gtggcgcggt attatcccgt attgacgccg    7080
ggcaagagca actcggtcgc cgcatacact attctcagaa tgacttggtt gagtactcac    7140
cagtcacaga aaagcatctt acggatggca tgacagtaag agaattatgc agtgctgcca    7200
taaccatgag tgataacact gcggccaact tacttctgac aacgatcgga ggaccgaagg    7260
agctaaccgc ttttttgcac aacatggggg atcatgtaac tcgccttgat cgttgggaac    7320
cggagctgaa tgaagccata ccaaacgacg agcgtgacac cacgatgcct gtagcaatgg    7380
caacaacgtt gcgcaaacta ttaactggcg aactacttac tctagcttcc cggcaacaat    7440
taatagactg gatggaggcg gataaagttg caggaccact tctgcgctcg gcccttccgg    7500
ctggctggtt tattgctgat aaatctggag ccggtgagcg tggaagccgc ggtatcattg    7560
cagcactggg gccagatggt aagccctccc gtatcgtagt tatctacacg acggggagtc    7620
aggcaactat ggatgaacga atagacaga tcgctgagat aggtgcctca ctgattaagc     7680
attggtaact gtcagaccaa gtttactcat atatacttta gattgattta aaacttcatt    7740
tttaatttaa aaggatctag gtgaagatcc tttttgataa tctcatgacc aaaatccctt    7800
aacgtgagtt ttcgttccac tgagcgtcag accccgtaga aaagatcaaa ggatcttctt    7860
gagatccttt ttttctgcgc gtaatctgct gcttgcaaac aaaaaaacca ccgctaccag    7920
cggtggtttg tttgccggat caagagctac caactctttt tccgaaggta actggcttca    7980
gcagagcgca gataccaaat actgtccttc tagtgtagcc gtagttaggc caccacttca    8040
agaactctgt agcaccgcct acatacctcg ctctgctaat cctgttacca gtggctgctg    8100
ccagtggcga taagtcgtgt cttaccgggt tggactcaag acgatagtta ccggataagg    8160
cgcagcggtc gggctgaacg gggggttcgt gcacacagcc cagcttggag cgaacgacct    8220
acaccgaact gagatacctac agcgtgagc tatgagaaag cgccacgctt cccgaaggga    8280
gaaaggcgga caggtatccg gtaagcggca gggtcggaac aggagagcgc acgagggagc    8340
ttccaggggg aaacgcctgg tatctttata gtcctgtcgg gtttcgccac ctctgacttg    8400
agcgtcgatt tttgtgatgc tcgtcagggg gcggagcct atggaaaaac gccagcaacg     8460
cggccttttt acggttcctg gccttttgct ggccttttgc tcacatgt               8508
```

<210> SEQ ID NO 29
<211> LENGTH: 20
<212> TYPE: DNA
<213> ORGANISM: Artificial Sequence
<220> FEATURE:
<223> OTHER INFORMATION: gRNA C35R

<400> SEQUENCE: 29
gacaaacact ccaccagcat                                               20

<210> SEQ ID NO 30
<211> LENGTH: 21
<212> TYPE: DNA
<213> ORGANISM: Artificial Sequence
<220> FEATURE:
<223> OTHER INFORMATION: gRNA C35L

<400> SEQUENCE: 30
gcccaatcca tcttctactc t                                             21

<210> SEQ ID NO 31
<211> LENGTH: 8088
<212> TYPE: DNA
<213> ORGANISM: Artificial Sequence
<220> FEATURE:
<223> OTHER INFORMATION: pCRISPR/Cas9n(D10A)DN

<400> SEQUENCE: 31

| | | | | | |
|---|---|---|---|---|---|
| gagggcctat | ttcccatgat | tccttcatat | ttgcatatac | gatacaaggc | tgttagagag | 60 |
| ataattggaa | ttaatttgac | tgtaaacaca | agatattag | tacaaaatac | gtgacgtaga | 120 |
| aagtaataat | ttcttgggta | gtttgcagtt | ttaaaattat | gttttaaaat | ggactatcat | 180 |
| gccaagtacg | cccctattg | acgtcaatga | cggtaaatgg | cccgcctggc | attgtgccca | 240 |
| gtacatgacc | ttatgggact | ttcctacttg | gcagtacatc | tacgtattag | tcatcgctat | 300 |
| taccatggtc | gaggtgagcc | ccacgttctg | cttcactctc | cccatctccc | cccctcccc | 360 |
| accccaatt | ttgtatttat | ttatttttta | attatttgt | gcagcgatgg | gggcgggggg | 420 |
| ggggggggg | cgcgcgccag | gcggggcggg | gcggggcgag | gggcggggcg | gggcgaggcg | 480 |
| gagaggtgcg | gcggcagcca | atcagagcgg | cgcgctccga | aagtttcctt | ttatggcgag | 540 |
| gcggcggcgg | cggcggccct | ataaaaagcg | aagcgcgcgg | cgggcgggag | tcgctgcgac | 600 |
| gctgccttcg | ccccgtgccc | cgctccgccg | ccgcctcgcg | ccgcccgccc | cggctctgac | 660 |
| tgaccgcgtt | actcccacag | gtgagcgggc | gggacggccc | ttctcctccg | ggctgtaatt | 720 |
| agctgagcaa | gaggtaaggg | tttaagggat | ggttggttgg | tggggtatta | atgtttaatt | 780 |
| acctggagca | cctgcctgaa | atcactttttt | ttcaggttgg | accggtgcca | ccatggacta | 840 |
| taaggaccac | gacggagact | acaaggatca | tgatattgat | tacaaagacg | atgacgataa | 900 |
| gatggcccca | aagaagaagc | ggaaggtcgg | tatccacgga | gtcccagcag | ccgacaagaa | 960 |
| gtacagcatc | ggcctggcca | tcggcaccaa | ctctgtgggc | tgggccgtga | tcaccgacga | 1020 |
| gtacaaggtg | cccagcaaga | aattcaaggt | gctgggcaac | accgaccggc | acagcatcaa | 1080 |
| gaagaacctg | atcggagccc | tgctgttcga | cagcggcgaa | acagccgagg | ccacccggct | 1140 |
| gaagagaacc | gccagaagaa | gatacaccag | acggaagaac | cggatctgct | atctgcaaga | 1200 |
| gatcttcagc | aacgagatgg | ccaaggtgga | cgacagcttc | ttccacagac | tggaagagtc | 1260 |
| cttcctggtg | gaagaggata | agaagcacga | gcggcacccc | atcttcggca | acatcgtgga | 1320 |
| cgaggtggcc | taccacgaga | agtaccccac | catctaccac | ctgagaaaga | aactggtgga | 1380 |
| cagcaccgac | aaggccgacc | tgcggctgat | ctatctggcc | ctggcccaca | tgatcaagtt | 1440 |
| ccggggccac | ttcctgatcg | agggcgacct | gaaccccgac | aacagcgacg | tggacaagct | 1500 |
| gttcatccag | ctggtgcaga | cctacaacca | gctgttcgag | gaaaacccca | tcaacgccag | 1560 |
| cggcgtggac | gccaaggcca | tcctgtctgc | cagactgagc | aagagcagac | ggctggaaaa | 1620 |
| tctgatcgcc | cagctgcccg | gcgagaagaa | gaatggcctg | ttcggcaacc | tgattgccct | 1680 |
| gagcctgggc | ctgaccccca | acttcaagag | caacttcgac | ctggccgagg | atgccaaact | 1740 |
| gcagctgagc | aaggacacct | acgacgacga | cctggacaac | ctgctggccc | agatcggcga | 1800 |
| ccagtacgcc | gacctgtttc | tggccgccaa | gaacctgtcc | gacgccatcc | tgctgagcga | 1860 |
| catcctgaga | gtgaacaccg | agatcaccaa | ggcccccctg | agcgcctcta | tgatcaagag | 1920 |
| atacgacgag | caccaccagg | acctgaccct | gctgaaagct | ctcgtgcggc | agcagctgcc | 1980 |
| tgagaagtac | aaagagattt | tcttcgacca | gagcaagaac | ggctacgccg | gctacattga | 2040 |

```
cggcggagcc agccaggaag agttctacaa gttcatcaag cccatcctgg aaaagatgga    2100
cggcaccgag gaactgctcg tgaagctgaa cagagaggac ctgctgcgga agcagcggac    2160
cttcgacaac ggcagcatcc cccaccagat ccacctggga gagctgcacg ccattctgcg    2220
gcggcaggaa gattttacc cattcctgaa ggacaaccgg gaaagatcg agaagatcct     2280 gaccttccgc atcccctact acgtgggccc tctggccagg ggaaacagca gattcgcctg    2340
gatgaccaga aagagcgagg aaaccatcac ccctggaac ttcgaggaag tggtggacaa     2400
gggcgcttcc gcccagagct tcatcgagcg gatgaccaac ttcgataaga acctgcccaa    2460
cgagaaggtg ctgcccaagc acagcctgct gtacgagtac ttcaccgtgt ataacgagct    2520
gaccaaagtg aaatacgtga ccgagggaat gagaaagccc gccttcctga gcggcgagca    2580
gaaaaaggcc atcgtggacc tgctgttcaa gaccaaccgg aaagtgaccg tgaagcagct    2640
gaaagaggac tacttcaaga aaatcgagtg cttcgactcc gtggaaatct ccggcgtgga    2700
agatcggttc aacgcctccc tgggcacata ccacgatctg ctgaaaatta tcaaggacaa    2760
ggacttcctg gacaatgagg aaaacgagga cattctggaa gatatcgtgc tgaccctgac    2820
actgtttgag gacagagaga tgatcgagga acggctgaaa acctatgccc acctgttcga    2880
cgacaaagtg atgaagcagc tgaagcggcg agatatacc ggctgggca ggctgagccg      2940 gaagctgatc aacggcatcc gggacaagca gtccggcaag acaatcctgg atttcctgaa    3000
gtccgacggc ttcgccaaca gaaacttcat gcagctgatc cacgacgaca gcctgacctt    3060
taaagaggac atccagaaag cccaggtgtc cggccagggc gatagcctgc acgagcacat    3120
tgccaatctg gccggcagcc ccgccattaa gaagggcatc ctgcagacag tgaaggtggt    3180
ggacgagctc gtgaaagtga tgggccggca caagcccgag aacatcgtga tcgaaatggc    3240
cagagagaac cagaccaccc agaagggaca gaagaacagc cgcgagagaa tgaagcggat    3300
cgaagagggc atcaaagagc tgggcagcca gatcctgaaa gaacaccccg tggaaaacac    3360
ccagctgcag aacgagaagc tgtacctgta ctacctgcag aatgggcggg atatgtacgt    3420
ggaccaggaa ctggacatca accggctgtc cgactacgat gtggaccata tcgtgcctca    3480
gagctttctg aaggacgact ccatcgacaa caaggtgctg accagaagcg acaagaaccg    3540
gggcaagagc gacaacgtgc cctccgaaga ggtcgtgaag aagatgaaga actactggcg    3600
gcagctgctg aacgccaagc tgattaccca gagaaagttc gacaatctga ccaaggccga    3660
gagaggcggc ctgagcgaac tggataaggc cggcttcatc aagagacagc tggtggaaac    3720
ccggcagatc acaaagcacg tggcacagat cctggactcc cggatgaaca ctaagtacga    3780
cgagaatgac aagctgatcc gggaagtgaa agtgatcacc ctgaagtcca gctggtgtc     3840 cgatttccgg aaggatttcc agttttacaa agtgcgcgag atcaacaact accaccacgc    3900
ccacgacgcc tacctgaacg ccgtcgtggg aaccgccctg atcaaaaagt accctaagct    3960
ggaaagcgag ttcgtgtacg gcgactacaa ggtgtacgac gtgcggaaga tgatcgccaa    4020
gagcgagcag gaaatcggca aggctaccgc caagtacttc ttctacagca acatcatgaa    4080 cttttttcaag accgagatta ccctggccaa cggcgagatc cggaagcggc ctctgatcga    4140
gacaaacggc gaaaccgggg agatcgtgtg ggataagggc cgggattttg ccaccgtgcg    4200
gaaagtgctg agcatgcccc aagtgaatat cgtgaaaaag accgaggtgc agacaggcgg    4260
cttcagcaaa gagtctatcc tgcccaagag aaacagcgat aagctgatcg ccagaaagaa    4320
ggactgggac cctaagaagt acggcggctt cgacagcccc accgtggcct attctgtgct    4380
ggtggtggcc aaagtggaaa agggcaagtc caagaaactg aagagtgtga aagagctgct    4440
```

```
gggatcacc atcatggaaa gaagcagctt cgagaagaat cccatcgact ttctggaagc    4500
caagggctac aaagaagtga aaaggacct gatcatcaag ctgcctaagt actccctgtt    4560
cgagctggaa aacggccgga agagaatgct ggcctctgcc ggcgaactgc agaagggaaa   4620
cgaactggcc ctgccctcca aatatgtgaa cttcctgtac ctggccagcc actatgagaa   4680
gctgaagggc tcccccgagg ataatgagca gaaacagctg tttgtggaac agcacaagca   4740
ctacctggac gagatcatcg agcagatcag cgagttctcc aagagagtga tcctggccga   4800
cgctaatctg gacaaagtgc tgtccgccta caacaagcac cgggataagc ccatcagaga   4860
gcaggccgag aatatcatcc acctgtttac cctgaccaat ctgggagccc tgccgccttt   4920
caagtacttt gacaccacca tcgaccggaa gaggtacacc agcaccaaag aggtgctgga   4980
cgccaccctg atccaccaga gcatcaccgg cctgtacgag acacggatcg acctgtctca   5040
gctgggaggc gacaaaggc cggcggccac gaaaaaggcc ggccaggcaa aaagaaaaa    5100 ggaattctaa ctagagctcg ctgatcagcc tcgactgtgc cttctagttg ccagccatct   5160
gttgtttgcc cctcccccgt gccttccttg accctggaag gtgccactcc cactgtcctt   5220
tcctaataaa atgaggaaat tgcatcgcat tgtctgagta ggtgtcattc tattctgggg   5280
ggtggggtgg ggcaggacag caaggggag gattgggaag agaatagcag gcatgctggg   5340
gagcggccgc aggaacccct agtgatggag ttggccactc cctctctgcg cgctcgctcg   5400
ctcactgagg ccgggcgacc aaaggtcgcc cgacgcccgg gctttgcccg ggcggcctca   5460
gtgagcgagc gagcgcgcag ctgcctgcag gggcgcctga tgcggtattt tctccttacg   5520
catctgtgcg gtatttcaca ccgcatacgt caaagcaacc atagtacgcg ccctgtagcg   5580
gcgcattaag cgcggcgggt gtggtggtta cgcgcagcgt gaccgctaca cttgccagcg   5640
ccctagcgcc cgctcctttc gctttcttcc cttcctttct cgccacgttc gccggctttc   5700
cccgtcaagc tctaaatcgg gggctccctt tagggttccg atttagtgct ttacggcacc   5760
tcgaccccaa aaaacttgat ttgggtgatg gttcacgtag tgggccatcg ccctgataga   5820
cggtttttcg ccctttgacg ttggagtcca cgttctttaa tagtggactc ttgttccaaa   5880
ctggaacaac actcaaccct atctcgggct attcttttga tttataaggg attttgccga   5940
tttcggccta ttggttaaaa aatgagctga tttaacaaaa atttaacgcg aattttaaca   6000
aaatattaac gtttacaatt ttatggtgca ctctcagtac aatctgctct gatgccgcat   6060
agttaagcca gccccgacac ccgccaacac ccgctgacgc gccctgacgg gcttgtctgc   6120
tcccggcatc cgcttacaga caagctgtga ccgtctccgg gagctgcatg tgtcagaggt   6180
tttcaccgtc atcaccgaaa cgcgcgagac gaaagggcct cgtgatacgc ctatttttat   6240
aggttaatgt catgataata atggtttctt agacgtcagg tggcactttt cggggaaatg   6300
tgcgcggaac ccctatttgt ttatttttct aaatacattc aaatatgtat ccgctcatga   6360
gacaataacc ctgataaatg cttcaataat attgaaaaag gaagagtatg agtattcaac   6420
atttccgtgt cgcccttatt ccctttttg cggcattttg ccttcctgtt tttgctcacc   6480
cagaaacgct ggtgaaagta aaagatgctg aagatcagtt gggtgcacga gtgggttaca   6540
tcgaactgga tctcaacagc ggtaagatcc ttgagagttt tcgccccgaa gaacgttttc   6600
caatgatgag cacttttaaa gttctgctat gtggcgcggt attatcccgt attgacgccg   6660
ggcaagagca actcggtcgc cgcatacact attctcagaa tgacttggtt gagtactcac   6720
cagtcacaga aaagcatctt acggatggca tgacagtaag agaattatgc agtgctgcca   6780
```

```
taaccatgag tgataacact gcggccaact tacttctgac aacgatcgga ggaccgaagg    6840
agctaaccgc ttttttgcac aacatggggg atcatgtaac tcgccttgat cgttgggaac    6900
cggagctgaa tgaagccata ccaaacgacg agcgtgacac cacgatgcct gtagcaatgg    6960
caacaacgtt gcgcaaacta ttaactggcg aactacttac tctagcttcc cggcaacaat    7020
taatagactg gatggaggcg gataaagttg caggaccact tctgcgctcg gcccttccgg    7080
ctggctggtt tattgctgat aaatctggag ccggtgagcg tggaagccgc ggtatcattg    7140
cagcactggg gccagatggt aagccctccc gtatcgtagt tatctacacg acggggagtc    7200
aggcaactat ggatgaacga atagacaga tcgctgagat aggtgcctca ctgattaagc     7260
attggtaact gtcagaccaa gtttactcat atatacttta gattgattta aaacttcatt    7320
tttaatttaa aaggatctag gtgaagatcc ttttttgataa tctcatgacc aaaatccctt    7380
aacgtgagtt ttcgttccac tgagcgtcag accccgtaga aaagatcaaa ggatcttctt    7440
gagatccttt ttttctgcgc gtaatctgct gcttgcaaac aaaaaaacca ccgctaccag    7500
cggtggtttg tttgccggat caagagctac caactctttt tccgaaggta actggcttca    7560
gcagagcgca gataccaaat actgtccttc tagtgtagcc gtagttaggc caccacttca    7620
agaactctgt agcaccgcct acatacctcg ctctgctaat cctgttacca gtggctgctg    7680
ccagtggcga taagtcgtgt cttaccgggt tggactcaag acgatagtta ccggataagg    7740
cgcagcggtc gggctgaacg gggggttcgt gcacacagcc cagcttggag cgaacgacct    7800
acaccgaact gagataccta cagcgtgagc tatgagaaag cgccacgctt cccgaaggga    7860
gaaaggcgga caggtatccg gtaagcggca gggtcggaac aggagagcgc acgagggagc    7920
ttccaggggg aaacgcctgg tatctttata gtcctgtcgg gtttcgccac ctctgacttg    7980
agcgtcgatt tttgtgatgc tcgtcagggg ggcggagcct atggaaaaac gccagcaacg    8040
cggccttttt acggttcctg gccttttgct ggccttttgc tcacatgt                  8088
```

<210> SEQ ID NO 32
<211> LENGTH: 44
<212> TYPE: DNA
<213> ORGANISM: Artificial Sequence
<220> FEATURE:
<223> OTHER INFORMATION: GJB-EX2-FU-f
<220> FEATURE:
<221> NAME/KEY: primer_bind
<222> LOCATION: (1)..(44)

<400> SEQUENCE: 32

```
tgactaattt ttttattta tgcagagcaa accgcccaga gtag                       44
```

<210> SEQ ID NO 33
<211> LENGTH: 20
<212> TYPE: DNA
<213> ORGANISM: Artificial Sequence
<220> FEATURE:
<223> OTHER INFORMATION: GJB-EX2-r
<220> FEATURE:
<221> NAME/KEY: primer_bind
<222> LOCATION: (1)..(20)

<400> SEQUENCE: 33

```
atgtctccgg taggccacgt                                                 20
```

<210> SEQ ID NO 34
<211> LENGTH: 23
<212> TYPE: DNA
<213> ORGANISM: Artificial Sequence

```
<220> FEATURE:
<223> OTHER INFORMATION: AF-INTRON-f
<220> FEATURE:
<221> NAME/KEY: primer_bind
<222> LOCATION: (1)..(23)

<400> SEQUENCE: 34
aggtaagtta ggcagggata ttc                                              23

<210> SEQ ID NO 35
<211> LENGTH: 27
<212> TYPE: DNA
<213> ORGANISM: Artificial Sequence
<220> FEATURE:
<223> OTHER INFORMATION: AF-INTRON-r
<220> FEATURE:
<221> NAME/KEY: primer_bind
<222> LOCATION: (1)..(27)

<400> SEQUENCE: 35
ctgcataaat aaaaaaatt agtcagc                                           27

<210> SEQ ID NO 36
<211> LENGTH: 38
<212> TYPE: DNA
<213> ORGANISM: Artificial Sequence
<220> FEATURE:
<223> OTHER INFORMATION: M3-GJ-f
<220> FEATURE:
<221> NAME/KEY: primer_bind
<222> LOCATION: (1)..(38)

<400> SEQUENCE: 36
gaagttcatc aagggcagct cactcaaagg cggtaata                              38

<210> SEQ ID NO 37
<211> LENGTH: 36
<212> TYPE: DNA
<213> ORGANISM: Artificial Sequence
<220> FEATURE:
<223> OTHER INFORMATION: M3-GJ-r
<220> FEATURE:
<221> NAME/KEY: primer_bind
<222> LOCATION: (1)..(36)

<400> SEQUENCE: 37
tcggtgaatt taaaactcga ggtgaagacg aaaggg                                36

<210> SEQ ID NO 38
<211> LENGTH: 21
<212> TYPE: DNA
<213> ORGANISM: Artificial Sequence
<220> FEATURE:
<223> OTHER INFORMATION: GJB-35delG-f
<220> FEATURE:
<221> NAME/KEY: primer_bind
<222> LOCATION: (1)..(21)

<400> SEQUENCE: 38
ctgggggtgt gaacaaacac t                                                21

<210> SEQ ID NO 39
<211> LENGTH: 21
<212> TYPE: DNA
<213> ORGANISM: Artificial Sequence
<220> FEATURE:
<223> OTHER INFORMATION: GJB-35delG-r
<220> FEATURE:
<221> NAME/KEY: primer_bind
```

```
<222> LOCATION: (1)..(21)

<400> SEQUENCE: 39
tttgttcaca cccccaggat c                                              21

<210> SEQ ID NO 40
<211> LENGTH: 22
<212> TYPE: DNA
<213> ORGANISM: Artificial Sequence
<220> FEATURE:
<223> OTHER INFORMATION: GJB-109G/A-f
<220> FEATURE:
<221> NAME/KEY: primer_bind
<222> LOCATION: (1)..(22)

<400> SEQUENCE: 40
tgatcctcat tgtggctgca aa                                             22

<210> SEQ ID NO 41
<211> LENGTH: 23
<212> TYPE: DNA
<213> ORGANISM: Artificial Sequence
<220> FEATURE:
<223> OTHER INFORMATION: GJB-109G/A-r
<220> FEATURE:
<221> NAME/KEY: primer_bind
<222> LOCATION: (1)..(23)

<400> SEQUENCE: 41
gcagccacaa tgaggatcat aat                                            23
```

COMPOSITION FOR EDITING A NUCLEIC ACID SEQUENCE AND METHOD USING THE SAME

RELATED APPLICATION

This application is a national phase application of PCT application No. PCT/US2017/067484, filed on Dec. 20, 2017, which claims priority from U.S. Provisional application No. 62/437,347 filed on Dec. 21, 2016, the contents of which are incorporated herein by reference.

SEQUENCE LISTING

The present application is being filed along with a Sequence Listing in electronic format. The Sequence Listing is provided as a file entitled 0750003WO_Sequence.TXT, created on May 27, 2019, which is 81,776 bytes in size. The information in the electronic format of Sequence Listing is incorporated herein by reference in its entirety.

BACKGROUND

1. Technical Field

The present disclosure relates to a composition and a method for editing a target genomic locus in cells in vitro, ex vivo or in vivo, and more particularly relates to a composition and a method for recombineering, genome modification, gene knockin, or gene knockout in eukaryotic cells.

2. Description of Associated Art

The bacterial genome editing has been well set and applied for knockin/knockout of bacterial genes, such as clustered regularly interspaced short palindromic repeats (CRISPR)-associated proteins (CRISPR/Cas), cre-lox system and Lambda Red system.

The Cre-lox system has been applied for gene modification of eukaryotic system for decades. The cre-lox system from bacteriophage has been mostly employed for genetically modified animals. A special sequence of lox is needed for a foreign fragment and a target organism that are recognized and homologous-recombined by Cre protein. The insertion fragment is a linearized DNA combined with a selection marker and/or a foreign gene and bi-capping with the lox sequence. For recombineering, the special sequence lox shall be created on the genome of target organisms in advance.

The CRISPR/Cas system is totally different from the cre-lox system. It is derived from bacterial self-defense and immunity memory from bacteriophages. A special sequence, like lox, is not necessary. The machine for CRISPR/Cas is a riboprotein complex composited by Cas proteins and a guidant RNA (gRNA). The guidant RNA carries a short homologous region (about 17 bp to 24 bp) to specifically target on the genome. The core Cas protein, Cas3 and Cas9 for type I and type II CRISPR, functions as a ribozyme to cleave DNA nearby the target sequence. This mechanism is broadly utilized in bacteria and archaea. Due to the composition of a Cas-gRNA complex, the type II CRISPR derived from *Synechococcus* sp. is simpler and easier for editing in other biological systems.

Currently, the cre-lox and CRISPR/Cas systems are the major tools for genome editing in a eukaryotic organism. However, limitations based on their mechanisms render time-consuming and low efficiency for genetic modification. The establishment of the cre-lox system in transgenic animals and the creation of the special sequence lox on a target organism are such big issues that the lox sequence is unusual at proposed sites in most organisms. By contrast, CRISPR/Cas is more superior and utilizes a user-designed sequence. The gRNA of CRISPR/Cas targets at a specific region designed by the user. However, the sequence of the gRNA is too short to be specified on the whole genome that would make a lot of non-specific targeting (i.e., the so-called off-target effects). In addition, the action of CRISPR in genome editing is completed through introducing double-strand breaking (DSB) by the core Cas protein and integrating a foreign fragment by non-homologous end joining (NHEJ). Nevertheless, the efficiency of NHEJ is very low, and the gene-modified cells cannot be selected directly and efficiently, which further limit the application of CRISPR/Cas.

The Lambda Red system is originally found in the study with regard to the recA gene of *Escherichia coli* (*E. coli*). In the recA-defective *E. coli* strain, a system encoded in the Lambda phage reveals about a 100-fold increase in recombination efficiency, while the recombination efficiency is declined in the recA+*E. coli* strain. Therefore, this system is named "Red" (Recombination defective) to differentiate from the recombination system in its *E. coli* host. The Lambda Red system comprises alpha, beta and gamma proteins, which function as an exonuclease, a single strand DNA (ssDNA) annealing protein and an inhibitor of the RecBCD complex, respectively. It is known that the Lambda Red recombination includes three major steps: (1) chewing a double-stranded DNA (dsDNA) from 5' to 3' by the alpha protein; (2) binding the sticky end of the dsDNA by the beta protein; and (3) annealing a single-stranded DNA (ssDNA) with a target sequence through RecA-invasion. The Lambda Red not only is able to construct a large DNA fragment containing a selection marker and/or foreign genes, but also highly specifies and recombines through capping both ends of the fragment with two homologous sequences at one or two different regions.

The Lambda Red recombineering had been constructed in a curable plasmid for single gene knockin/knockout in *E. coli*. Recently, it has also been employed to genome editing of *Bacillus subtilis* (*Bs. subtilis*). Also, similar systems have been found from other bacteriophages and proven their efficiency of recombination in prokaryotic. However, as an urgent requirement of genome editing in over-species or multiple biology systems, it is still an important issue to provide a more direct, efficient and precise method for genome editing by utilizing the Lambda Red and its relative phage recombination systems in eukaryote cells and organisms, including plants, animals and human.

SUMMARY

In view of the foregoing, the present disclosure provides a composition for editing a target nucleic acid sequence in cells in vitro, ex vivo or in vivo, comprising: one or more nucleic acid molecules each comprising an artificial nucleic acid sequence flanked with capping sequences; and Lambda beta protein or a vector comprising a nucleic acid sequence encoding the Lambda beta protein.

Each of the capping sequences is homologous to a region in the target nucleic acid sequence. The target nucleic acid sequence may be an exon or an intron, depending on purposes, such as knockin, knockout, in-frame insertion, genome modification, or recombineering. Furthermore, the artificial nucleic acid sequence may be an intron sequence. Moreover, the artificial nucleic acid sequence may comprise a selection marker to allow a direct, efficient and precise selection for an integrant in genome. In addition, the vector may further comprise a promoter operably linked to the nucleic acid sequence encoding the Lambda beta protein and at least one selected from the group consisting of a nucleic acid sequence encoding exonuclease, a nucleic acid sequence encoding anti-RecBCD protein, and a reporter gene.

In one embodiment of the present disclosure, the composition further comprises at least one of exonuclease and anti-RecBCD protein. In another embodiment of the present disclosure, the composition is used in combination with at least one chosen from zinc-finger nucleases (ZFNs) system, transcription activator-like effector nucleases (TALENs) system and clustered regularly interspaced short palindromic repeat (CRISPR)/Cas system.

According to another embodiment, the present disclosure further provides a method for editing a target nucleic acid sequence in cells in vitro, ex vivo or in vivo. The method comprises introducing the aforesaid composition into the cells for a genetic change in the target locus to be induced. The method further comprises culturing the cells under a condition suitable for inducing homologous recombination between the nucleic acid molecule and the target nucleic acid sequence. In one embodiment of the present disclosure, the Lambda beta protein introduced into the cells or encoded by the vector in the cells binds to the nucleic acid molecule, and further promotes annealing between the capping sequence of the nucleic acid molecule and the region in the target nucleic acid sequence to form a recombinant in the cells. Moreover, the artificial nucleic acid sequence as an intron sequence would be removed by RNA splicing during maturation of the RNA product of the target nucleic acid sequence with the genetic change in the cell. In one embodiment of the present disclosure, the cells with the genetic change may be detected and cloned based on the selection marker.

In summary, the present disclosure provides a composition for simultaneously targeting nucleic acid sequence and providing intron selection (intron including a selection marker) in cells in vitro, ex vivo or in vivo. Also, the present disclosure provides a more direct, efficient and precise method for editing a target locus in cells for such as recombineering, genome modification, gene knockin, and gene knockout. Moreover, the cells may be eukaryotic cells, including but not limited to mammalian cells such as human cells and human induced pluripotent stem cells.

BRIEF DESCRIPTION OF THE DRAWINGS

The present disclosure can be more fully understood by reading the following detailed descriptions of the embodiments, with reference made to the accompanying drawings.

DETAILED DESCRIPTION OF THE EMBODIMENTS

Figure 1A:
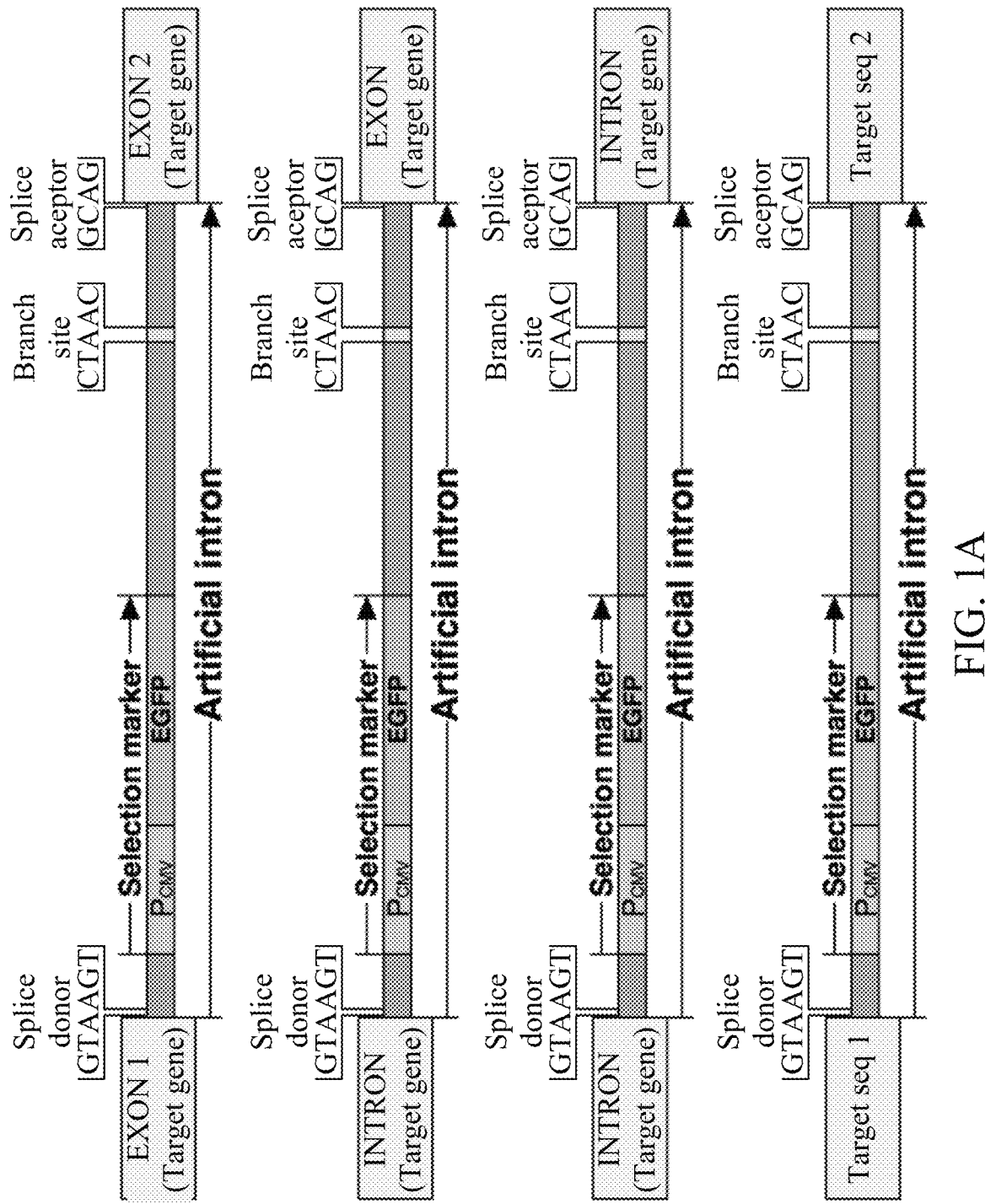
FIG. 1A shows the deployment of a nucleic acid molecule comprising an artificial nucleic acid sequence flanked with capping sequences.

The following specific examples are used to exemplify the present disclosure. A person of ordinary skill in the art can conceive the other advantages of the present disclosure, based on the disclosure of the specification. The present disclosure can also be implemented or applied as described in different specific examples. It is possible to modify and/or alter the above examples for carrying out this disclosure without contravening its spirit and scope, for different aspects and applications.

Provided is a composition for editing a target nucleic acid sequence in cells in vitro, ex vivo or in vivo. The composition comprises: one or more nucleic acid molecules each comprising an artificial nucleic acid sequence flanked with capping sequences; and Lambda beta protein or a vector comprising a nucleic acid sequence encoding the Lambda beta protein.

The composition of the present disclosure can be used for simultaneously targeting nucleic acid sequence and providing intron selection in cells in vitro, ex vivo or in vivo. As used herein, the term "intron selection" is to be interpreted as the process of using an artificial intron sequence including a selection maker for genetic engineering.

In an embodiment of the present disclosure, the vector is a circular plasmid or a linear DNA.

In an embodiment of the present disclosure, each capping sequence is homologous to a region in the target nucleic acid sequence. In another embodiment of the present disclosure, the region in the target nucleic acid sequence is an exon or an intron.

In an embodiment of the present disclosure, each capping sequence independently has 10 to 5000 nucleotides in length; for example, the length range of each capping sequence is selected from the group consisting of 10-500, 500-1000, 1000-1500, 1500-2000, 2000-2500, 2500-3000, 3000-3500, 3500-4000, 4000-4500, and 4500-5000 nucleotides. In another embodiment of the present disclosure, both of the capping sequences have 10-500 nucleotides in length.

In an embodiment of the present disclosure, the vector may comprise a promoter operably linked to the nucleic acid sequence encoding the Lambda beta protein. In another embodiment of the present disclosure, the promoter is a constitutive promoter such as cytomegalovirus (CMV) promoter, an inducible promoter such as tetracycline-inducible promoter (tetracycline On and Off systems), or a cell or tissue-specific promoter such as dopamine neuron-specific promoter (tyrosine hydroxylase promoter), astrocyte-specific promoter (GFAP promoter) and sensory hair cells-specific promoter (Myo7A promoter).

In an embodiment of the present disclosure, the vector further comprises at least one selected from the group consisting of a nucleic acid sequence encoding exonuclease, a nucleic acid sequence encoding anti-RecBCD protein, and a reporter gene. In another embodiment of the present disclosure, the exonuclease is 5' to 3' exonuclease, such as T5 or Lambda exonuclease. In yet another embodiment of the present disclosure, the reporter gene is a fluorescent reporter gene, an enzymatic reporter gene or an antibiotic selection gene.

In an embodiment of the present disclosure, the vector comprises a promoter, a nucleic acid sequence encoding Lambda beta protein, a nucleic acid sequence encoding Lambda exonuclease, and a reporter gene. In another embodiment of the present disclosure, the vector (either a circular plasmid or a linear DNA), in 5' to 3' downstream direction, comprises: a promoter, a nucleic acid sequence encoding Lambda beta protein, a nucleic acid sequence encoding Lambda exonuclease, and a reporter gene. It can be understood that the Lambda exonuclease may be replaced with other 5' to 3' exonuclease in another embodiment of the present disclosure.

In an embodiment of the present disclosure, the artificial nucleic acid sequence is an intron sequence. In another embodiment of the present disclosure, the artificial nucleic acid sequence comprises a splice donor site, a splice acceptor site, and a branch site.

In an embodiment of the present disclosure, the nucleic acid molecule is a single-stranded DNA or a double-stranded DNA. In one embodiment, the nucleic acid molecule is a double-stranded DNA. In another embodiment, the nucleic acid molecule is a polymerase chain reaction (PCR) product.

In an embodiment of the present disclosure, the artificial nucleic acid sequence comprises a selection marker. In another embodiment of the present disclosure, the selection marker comprises a promoter operably linked to a reporter gene. In another embodiment of the present disclosure, the reporter gene is a fluorescent reporter gene, an enzymatic reporter gene or an antibiotic resistance gene, and the promoter is a constitutive promoter such as cytomegalovirus (CMV) promoter, an inducible promoter such as tetracycline-inducible promoter (tetracycline On and Off systems), or a cell or tissue-specific promoter such as dopamine neuron-specific promoter (tyrosine hydroxylase promoter), astrocyte-specific promoter (GFAP promoter) and sensory hair cells-specific promoter (Myo7A promoter).

In an embodiment of the present disclosure, the nucleic acid molecule is present in the composition in an amount of from 0.05 μg to 5 μg. In an embodiment, the amount of the nucleic acid molecule has a lower limit chosen from 0.05, 0.06, 0.1, 0.12, 0.15 and 0.2 μg and an upper limit chosen from 0.25, 0.5, 1, 1.2, 1.5 and 2.5. In another embodiment of the present disclosure, the nucleic acid molecule is present in the composition in an amount of from 0.05 μg to 1.5 μg. In yet another embodiment of the present disclosure, the nucleic acid molecule is present in the composition in an amount of from 0.1 μg to 1.5 μg. In yet a further embodiment of the present disclosure, the nucleic acid molecule is present in the composition in an amount of from 0.12 μg to 1.2 μg. A person skilled in the art can understand that the amount of the nucleic acid molecule may be adjusted depending on the cell density.

In an embodiment of the present disclosure, the weight ratio of the nucleic acid molecule to the vector is from 2:1 to 1:10, such as from 1:1 to 1:8.

In an embodiment of the present disclosure, the composition further comprises exonuclease or anti-RecBCD protein. In another embodiment of the present disclosure, the exonuclease is 5' to 3' exonuclease, such as T5 or Lambda exonuclease. In yet another embodiment of the present disclosure, the composition further comprises Lambda exonuclease and/or anti-RecBCD protein.

In an embodiment of the present disclosure, the composition further comprises ZFN, TALEN or CRISPR/Cas system. In another embodiment of the present disclosure, the composition is used in combination with at least one chosen from ZFN, TALEN and CRISPR/Cas systems.

According to a further embodiment of the present disclosure, the present disclosure provides a method for editing a target nucleic acid sequence in cells in vitro, ex vivo or in vivo. The method comprises introducing the aforesaid composition into the cells for a genetic change in the target nucleic acid sequence to be induced.

In an embodiment of the present disclosure, after introducing the aforesaid composition into the cells, the nucleic acid molecule is bound to the Lambda beta protein introduced or encoded by the vector in the cells. Further, the Lambda beta protein promotes annealing between the capping sequence of the nucleic acid molecule and the region in the target nucleic acid sequence, to which the capping sequence is homologous, to form a recombinant. In an embodiment of the present disclosure, the cells are cultured under a condition suitable for inducing homologous recombination between the nucleic acid molecule and the target nucleic acid sequence.

In an embodiment of the present disclosure, the artificial nucleic acid sequence is an intron sequence that may be removed by RNA splicing during maturation of the RNA product of the target nucleic acid sequence with the genetic change in the cells.

In an embodiment of the present disclosure, the editing of the target nucleic acid sequence is at least one selected from the group consisting of recombineering, genome modification, gene knockin, and gene knockout.

In an embodiment of the present disclosure, the cells may be eukaryotic cells. In one embodiment, the eukaryotic cells may be mammalian cells. In another embodiment, the mammalian cells may be human cells. In still another embodiment, the human cells are stem cells such as induced pluripotent stem cells (iPSCs) or trans-differentiated cells such as induced neurons or induced cardiomyocytes.

EXAMPLE

Strain and Culture Medium

The bacteria strain *Escherichia coli* DH5a (Yeastern Biotech Co., Ltd) was used to harbor cloning vectors and constructions. *E. coli* DH5a was cultured in Luria-bertani broth composited by 0.5% yeast extract (DIFCO, USA), 1% tryptone (DIFCO, USA), 1% NaCl (First Chemicals, Taiwan). For selection and maintaining plasmids, 100 µg/ml Ampicillin was applied in culturing recombinant *E. coli*.

Culture of Human Embryonic Kidney (HEK293T) Cells

The human embryonic kidney (HEK293T) cells (ATCC® CRL-3216™) were maintained in Dulbecco's modified Eagle's medium (DMEM, GIBCO), containing 10% fetal bovine serum (FBS, GIBCO), 1% penicillin and streptomycin solution (GIBCO) at 37° C. in a 5% $CO_2$ incubator. Cells were split twice per week.

Generation of Human Induced Pluripotent Stem Cells (hiPSCs)

Human iPSCs were generated from normal human dermal fibroblasts (NHDF, PromoCell). The iPSCs were reprogrammed by the transduction of retroviral vectors encoding four transcription factors, as described previously (Maekawa et al., Nature, 2011, 474(7350):225-9). Briefly, the plasmids pMXs-OCT4, SOX2, KLF4, and GLIS1 (Addgene) were individually packaged into retroviral particles by transfection into fibroblasts using the TransIT-X2 (Mirus). Retroviral transduction was performed two times at one-day intervals. After 1 week of transduction, $1 \times 10^5$ infected fibroblasts were re-seeded on inactivated murine embryonic fibroblast (MEF) feeder cells. The primary culture of MEF cells was described previously (Lei Y, Methods Mol. Biol., 2013, 1031:59-64). The following day, the medium was replaced with human embryonic stem cells (hESCs) medium and changed every day. After 21 to 28 days of re-seeding, the colonies were each transferred to feeder cultures in organ culture dishes (ODC; BD) to develop additional colonies for characterization.

DNA Transfections

All DNA constructs used were propagated in *E. coli*, and isolated by Midi plasmid kit (Geneaid). Transfection of HEK293T cells and iPSCs was achieved by using TransITX2 and TransIT-LT1 (Mirus), respectively. According to the user manual, 80% confluent of HEK293T cells was required in each transfection containing 7.5 µl of TransITX2 and 2.5 µg of DNA per well in 6-well plate format. Furthermore, the transfection condition of human iPSCs was listed: $2 \times 10^6$ cells, 4 µg of DNA and 12 µl of TransIT-LT1 in each transfection.

Example 1: Construction of Plasmids pAB-mCherry, pAB and pAF-INTRON

Figure 1B:
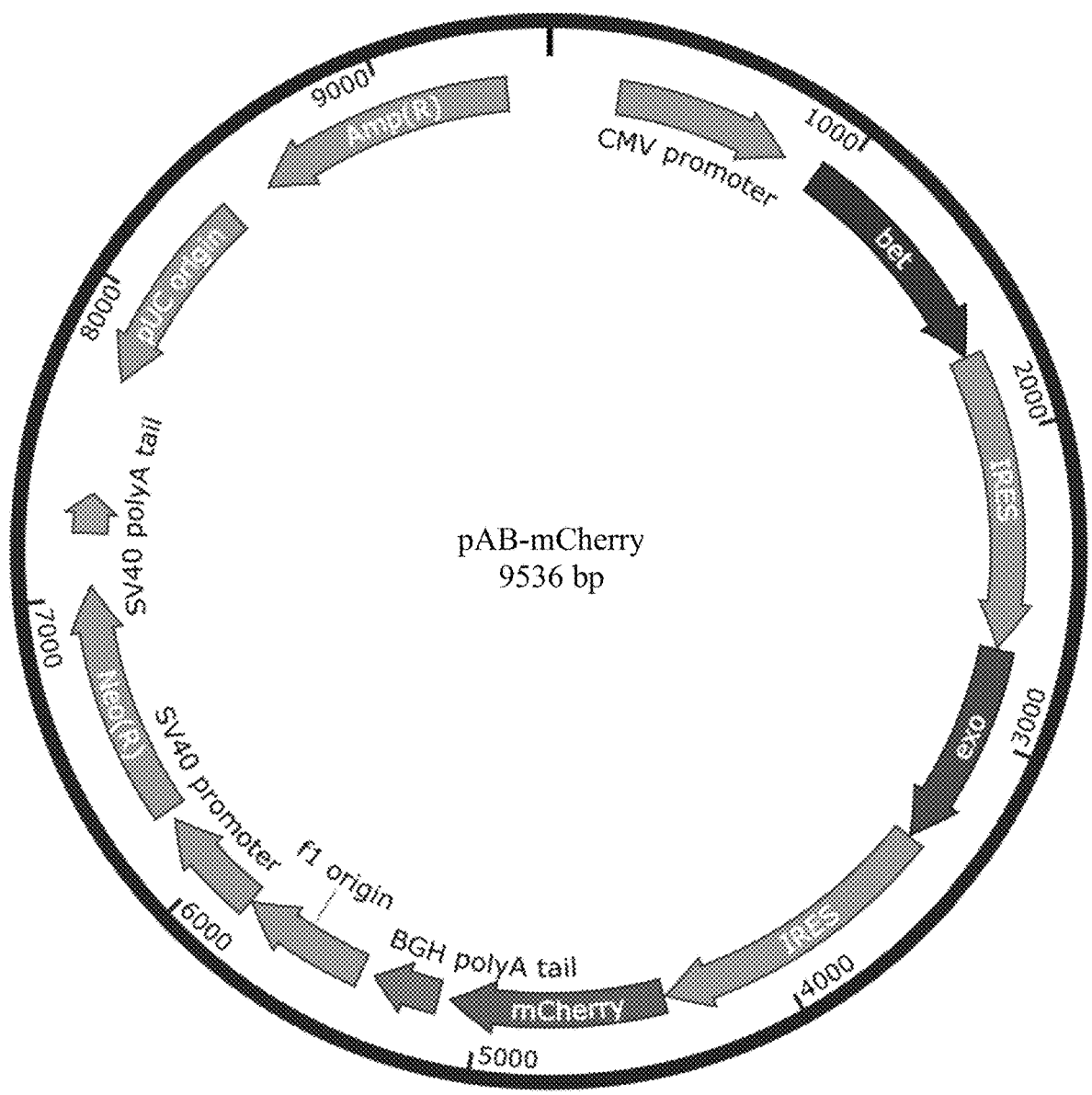
FIG. 1B shows the construction of plasmid pAB-mCherry.

For construction of the plasmid pAB-mCherry (FIG. 1B, created with SnapGene®), PCR primers were designed to amplify bet and exo genes from the plasmid pKD46 (*Coli* Genetics Stock Center, CGSC) carrying the λ-red system, IRES sequences from plasmid pRECIVER-L122 (Genecopoeia) and the backbone of pcDNA3.1-mCherry (Genecopoeia). All PCR products were purified and ligated at 50° C. by one-step ISO DNA assembly (Gibson D G, Methods Enzymol., 2011, 498:349-61). The sequence of pAB-mCherry was represented by SEQ ID NO. 1.

The mCherry-free plasmid pAB was derived from pAB-mCherry with the mCherry gene being removed by XbaI digestion, followed by self ligation. A disable plasmid pAB$^{DN}$ as negative control was constructed by removing the CMV promoter from the plasmid pAB by SpeI-NheI digestion.

For construction of the plasmid pAF-INTRON, which was used in preparation of a nucleic acid molecule comprising an artificial nucleic acid sequence flanked with capping sequences in one embodiment of the present disclosure, the CMV promoter and EGFP gene from pRE-CEIVER-LV122 were sub-cloned into the plasmid pQE70 (QIAGEN) as the plasmid pQE-EGFP by PCR amplifying and one-step ISO DNA assembly. All of the splicing points, splicing donor and acceptor, and branch points were created by a site-directed mutagenesis method (Kunkel T A, Proc. Natl. Acad. Sci. USA, 1985, 82:488-92). The construction was transformed into *E. coli* DH5a, and confirmed to have all artificial splicing points by DNA sequencing. The resulting sequence of the pAF-INTRON was represented by SEQ ID NO. 2.

Example 2: Preparation of GJB2-EX-AF, GJB2-EX35-AF and GJB2-EX109-AF

Exons 1 and 2 of the GJB2 gene were separately amplified from the genomic DNA of human HEK293T cells. Linearized artificial intron was prepared from plasmid pAF-INTRON by PCR. GJB2 Exons 1 and 2 and linearized artificial intron were assembled by one-step isothermal DNA assembly and sub-cloned into plasmid pQE70 as the plasmid pQE-GJB2-EXAF. A deletion mutation (c.35 delG) or point mutation from G to A (c.109 G>A) on Exon 2 of the GJB2 gene was created from the plasmid pQE-GJB2-EXAF through PCR, and DpnI eliminated the original plasmid template, so as to obtain the plasmids pQE-GJB2-EX35AF and pQE-GJB2-EX109AF. Exon 2 of the GJB2 gene, which was normal or contained mutation c.35delG or c.109G>A, was represented by SEQ ID NOs. 3-5, respectively.

Figure 4A:
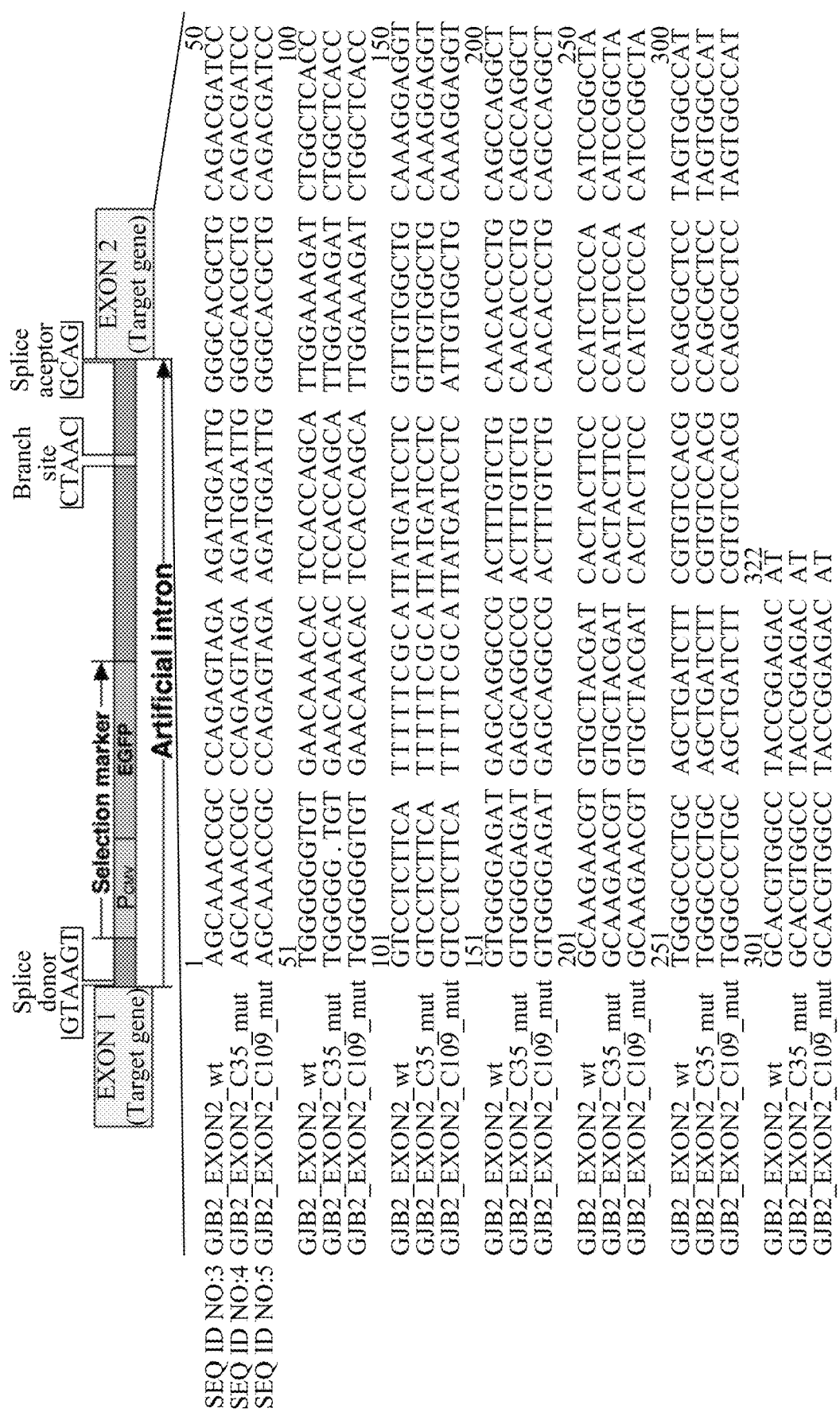
FIG. 4A is a schematic description of artificial intron flanked with Exon 1 and Exon 2 of the GJB2 gene. GJB2_EXON2_wt represents normal Exon 2 of the GJB2 gene; GJB2_EXON2_c35_mut represents the c.35delG mutation in Exon 2 of the GJB2 gene; and GJB2_EXON2_c109_mut represents the c. 109G>A mutation in Exon 2 of the GJB2 gene.

For enrichment of the linearized GJB2-EX-AF, GJB2-EX35-AF and GJB2-EX109-AF, PCR amplification from plasmids pQE-GJB2-EXAF, pQE-GJB2-EX35AF and pQE-GJB2-EX109AF was performed with primers for cloning Exons 1 and 2 of the GJB2 gene (FIG. 4A). The sequences of GJB2-EX-AF, GJB2-EX35-AF and GJB2-EX109-AF were represented by SEQ ID NOs. 6-8, respectively.

The sequences of the primers used in Examples 1 and 2 were listed in Table 1 below.

TABLE 1

| Plasmid | Primer | Sequence (5' to 3') | SEQ ID NO. |
|---|---|---|---|
| pAB-mCherry | CMVpro-r | GCA GTA CTC ATG GTG GCG AGC TCG GTA CCA AGC TTA AGT | 9 |
| | cher-f | AGA CGA CCT TCC GCC ACC ATG GTG AGC AAG GGC GAG GAG | 10 |

TABLE 1-continued

| Plasmid | Primer | Sequence (5' to 3') | SEQ ID NO. |
|---|---|---|---|
| | bet-f | CTT GGT ACC GAG CTC GCC ACC ATG AGT ACT GCA CTC GCA ACG | 11 |
| | bet-r | CCG CGG ATC TCA CTA TCA TGC TGC CAC CTT CTG CTC T | 12 |
| | IRES-I-f | AAG GTG GCA GCA TGA TAG TGA GAT CCG CGG CCG CA | 13 |
| | IRES-I-r | CGG TGT CAT GGT GGC GGA AGG TCG TCT CCT TGT GGG | 14 |
| | exo-f | AGA CGA CCT TCC GCC ACC ATG ACA CCG GAC ATT ATC CTG C | 15 |
| | exo-r | GCC GCG GAT CTC TAG ATC ATC GCC ATT GCT CCC CAA AT | 16 |
| | IRES-II-f | GAG CAA TGG CGA TGA TCT AGA GAT CCG CGG CCG CA | 17 |
| | IRES-II-r | CCT TGC TCA CCA TGG TGG CGG AAG GTC GTC TCC TTG TGG G | 18 |
| pAF-INTRON | EB-VEC-f | ACG CCT GGG GTA ATG ACT CTC T | 19 |
| | EB-VEC-r | CTC GAG GTG AAG ACG AAA GGG | 20 |
| | L122-VEC-f | CCC TTT CGT CTT CAC CTC GAG GTA AGT TAG GCA GGG ATA TTC ACC AT | 21 |
| | L122-U-r | TCC CTA GTT AGC GAG AGA GCT CCC A | 22 |
| | L122-D-f | GGG AGC TCT CTC GCT AAC TAG GGA A | 23 |
| | L122-VEC-r | AGA GAG TCA TTA CCC CAG GCG TCT GCA TAA ATA AAA AAA ATT AGT CAG C | 24 |
| pQE-GJB2-EXAF | GJB-EX1-f | GGG GTG CGG TTA AAA GGC G | 25 |
| | GJB-EX1-FU-r | GTG AAT ATC CCT GCC TAA CTT ACC TGC GTC GGG AGG AAG C | 26 |
| | GJB-EX2-FU-f | TGA CTA ATT TTT TTT ATT TAT GCA GAG CAA ACC GCC CAG AGT AG | 32 |
| | GJB-EX2-r | ATG TCT CCG GTA GGC CAC GT | 33 |
| | AF-INTRON-f | AGG TAA GTT AGG CAG GGA TAT TC | 34 |
| | AF-INTRON-r | CTG CAT AAA TAA AAA AAA TTA GTC AGC | 35 |
| | M3-GJ-f | GAA GTT CAT CAA GGG CAG CTC ACT CAA AGG CGG TAA TA | 36 |
| | M3-GJ-r | TCG GTG AAT TTA AAA CTC GAG GTG AAG ACG AAA GGG | 37 |
| Mutation c.35delG | GJB-35delG-f | CTG GGG GTG TGA ACA AAC ACT | 38 |
| | GJB-35delG-r | TTT GTT CAC ACC CCC AGG ATC | 39 |
| Mutation c.109G > A | GJB-109G/A-f | TGA TCC TCA TTG TGG CTG CAA A | 40 |
| | GJB-109G/A-r | GCA GCC ACA ATG AGG ATC ATA AT | 41 |

Example 3: Co-Transfection of Plasmid pAB-mCherry and GJB2-EX-AF into Human HEK293T Cells and iPSC Cells Human HEK293T and iPSC cells were transfected with pAB-mCherry and GJB2-EX-AF in different ratios, and cultured in 6-well plates for 48 hours. The results were observed by fluorescence microscopy. Further, recombination efficiency was analyzed by flow cytometry.

Observation by Fluorescence Microscopy

Figure 2A:
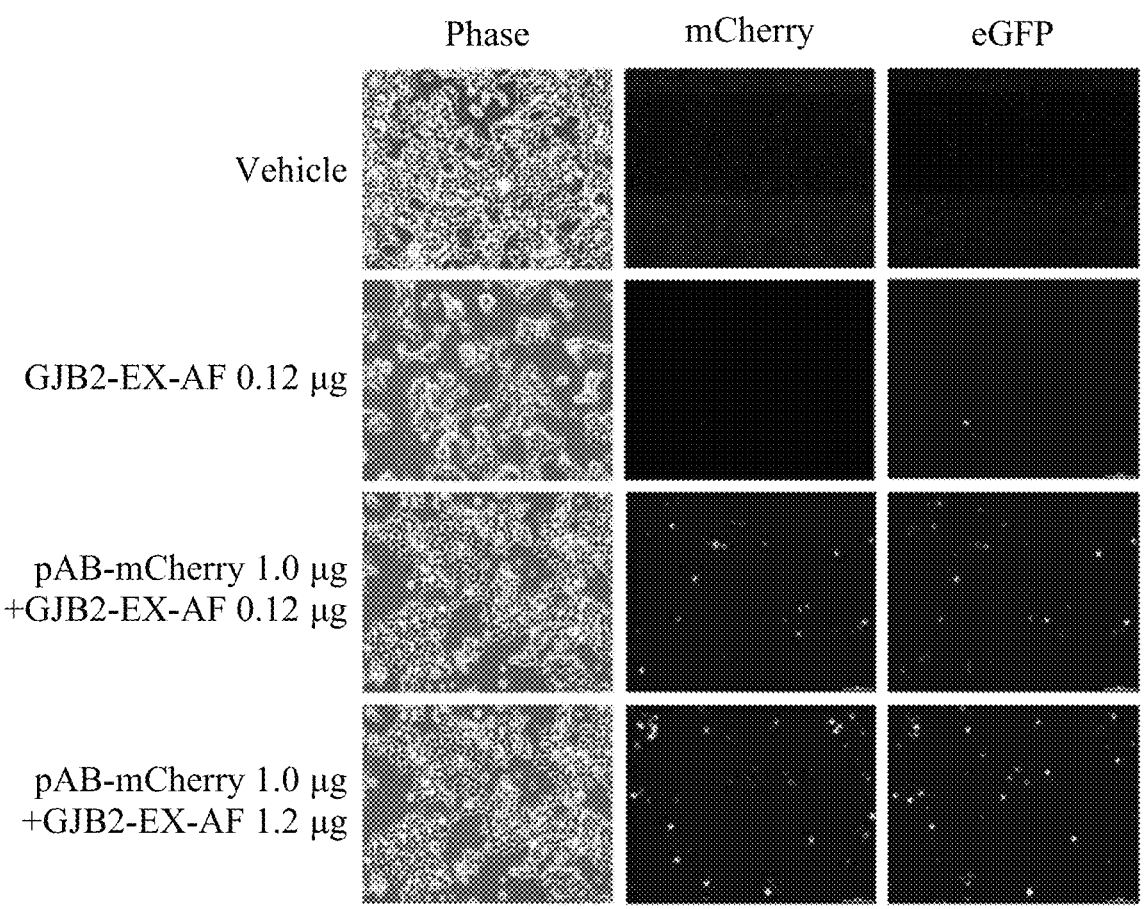
FIGS. 2A to 2C show a result chart of human HEK293T cells co-transfected with GJB2-EX-AF and plasmid pAB-mCherry in different ratios for 48 hours, which were observed by fluorescence microscopy (FIG. 2A) or flow cytometry (FIG. 2B), and quantitated based on the EGFP-positive cells evaluated by flow cytometry (FIG. 2C). Data are presented as mean±sem, *p<0.05, **p<0.01, n=5.
Figure 3:
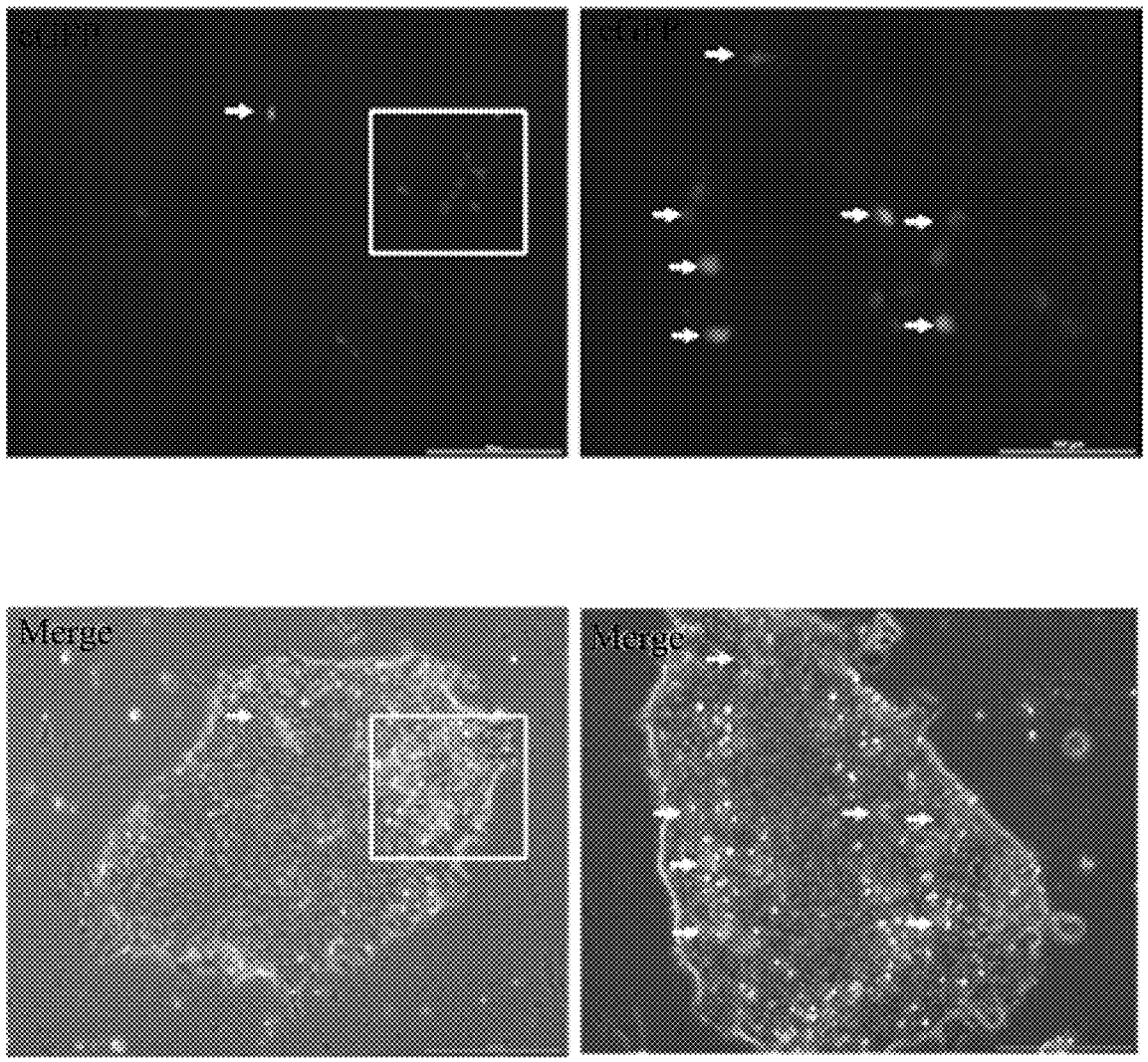
FIG. 3 is a result chart of human induced pluripotent stem cells (iPSCs) co-transfected with GJB2-EX-AF and plasmid pAB-mCherry for 48 hours. Two independent human iPSC clones (Left and Right panels) with eGFP green fluorescence are indicated by white box and arrows. Scale bar: 100 μm.

As shown in FIG. 2A, most of HEK293T cells expressed eGFP, which was encoded by the EGFP embedded in the artificial intron in GJB2-EX-AF driven by the CMV promoter. Furthermore, the expression of eGFP in two independent human iPSC clones was also observed (FIG. 3).

Therefore, these results indicated the occurrence of recombination between GJB2-EX-AF and the target locus in both of human HEK293T cells and iPS cells.

Flow Cytometry Analysis

In order to further evaluate the recombination efficiency, quantitative analysis was performed by using flow cytometry. Specifically, all analyses were performed using a SH800 Cell Sorting System (Sony), made available through the Core Facility for Flow Cytometry at MacKay Memorial Hospital (New Taipei City, Taiwan). Data analysis was performed by using SH800 software (Sony). Dead cells and debris were excluded from analysis based on forward angle and side scatter light gating. Whenever possible, 10,000 gated events were collected for analysis.

Figure 2B:
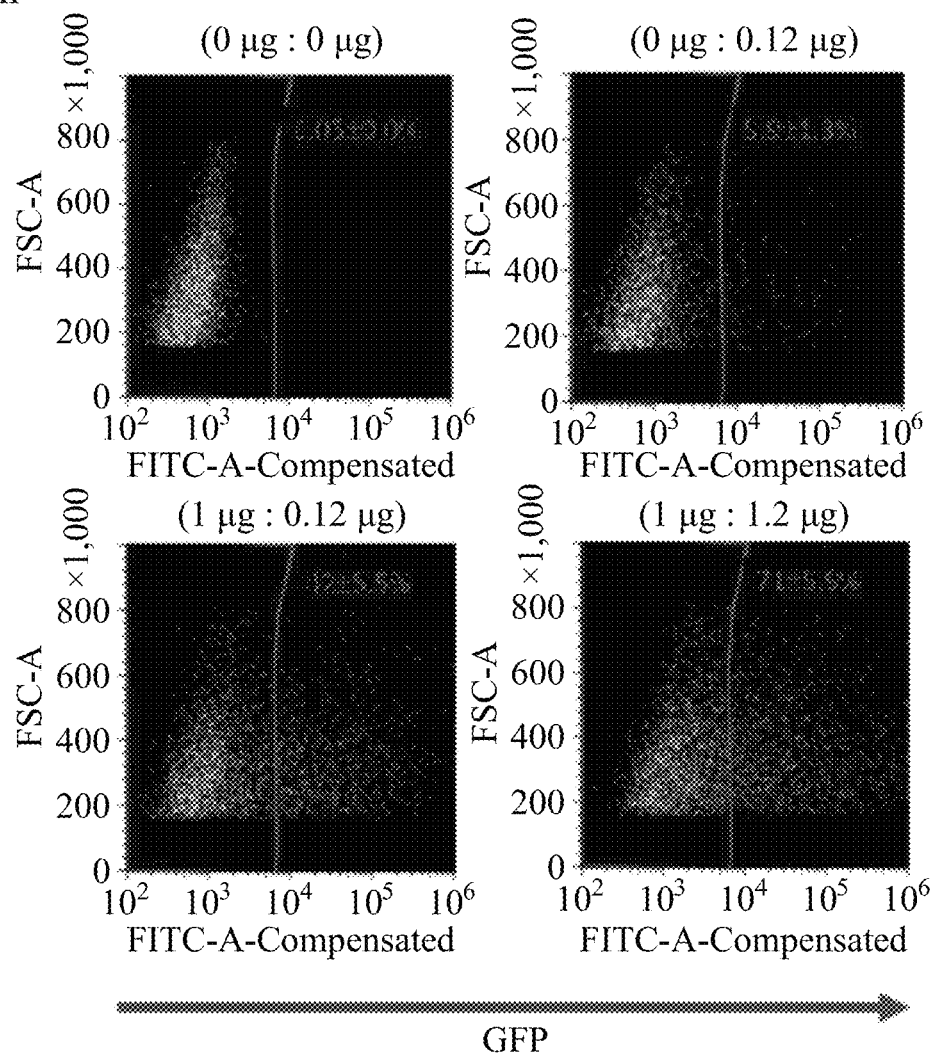
Figure 2C:
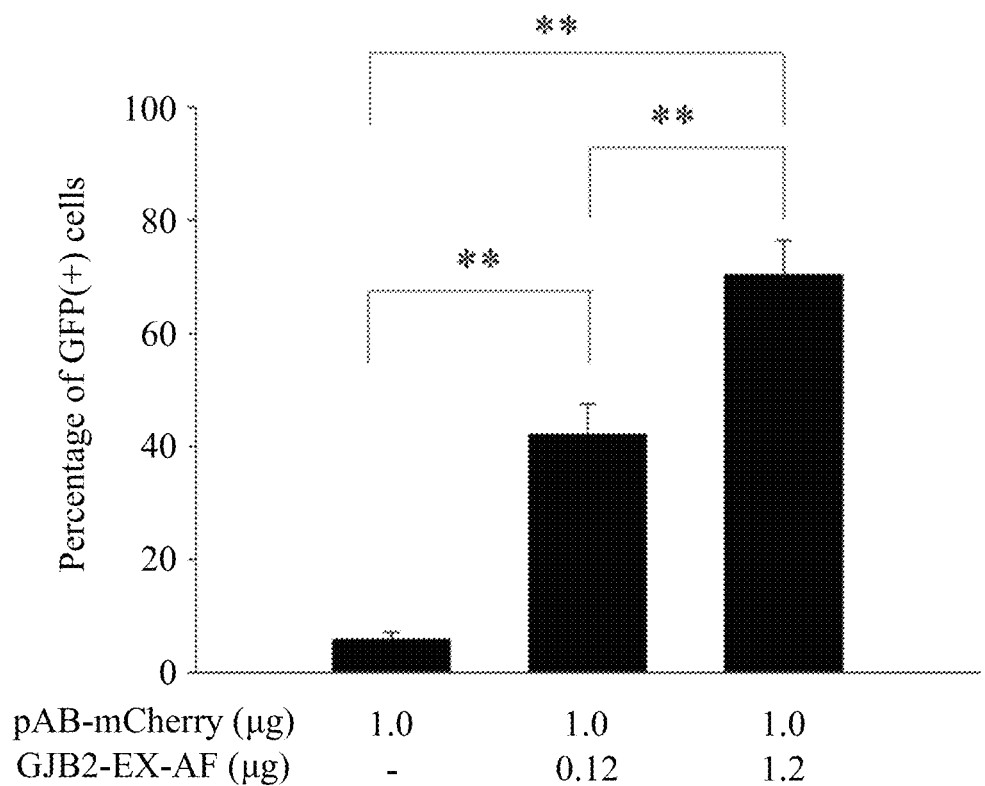

Table 2, FIGS. 2B and 2C presented recombination efficiencies in human HEK293T cells at different ratios of pAB-mCherry to GJB2-EX-AF.

TABLE 2

|  | (pAB-mCherry:GJB2-EX-AF) | |
| --- | --- | --- |
|  | (1 μg:0.12 μg) | (1 μg:1.2 μg) |
| EGFP-positive cell (%) | 42% | 71% |

Figure 2D:
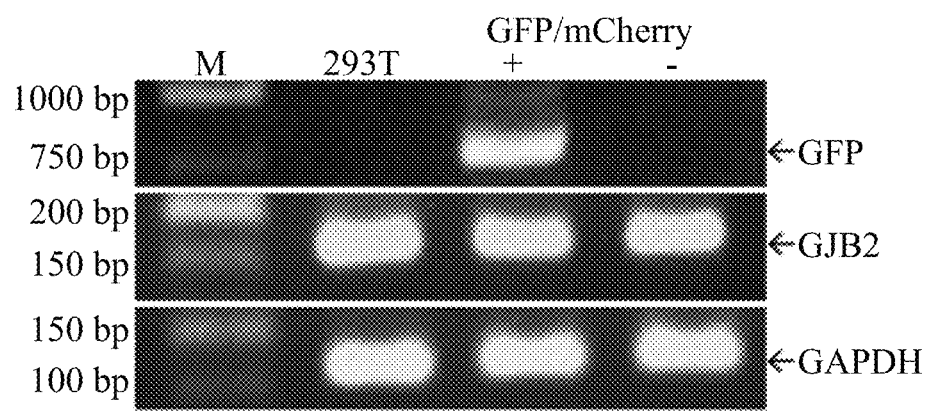
FIG. 2D shows the electrophoresis results of PCR amplification of the EGFP gene and GJB2 gene from DNA of HEK293T cells co-transfected with GJB2-EX-AF and plasmid pAB-mCherry.

In addition, the EGFP(+)/mCherry(+) cells among the human HEK293T cells transfected with 1 μg pAB-mCherry and 0.12 μg GJB2-EX-AF were sorted for the validation of GJB2-EX-AF integration into GJB2 genomic locus and the analysis of endogenous GJB2 mRNA expression by RT-PCR. As shown in FIG. 2D, the result indicated that the pAB recombineering system did not interfere endogenous mRNA expression of GJB2 gene in HEK293T cells.

Example 4: Co-Transfection of Plasmid pAB-mCherry with GJB2-EX35-AF and with GJB2-EX109-AF into Human HEK293T Cells GJB2-EX35-AF and GJB2-EX109-AF were designed to contain c.35delG or c.109G>A mutations in Exon 2 of the GJB2 gene, respectively, as described in Example 2. The c.35delG and c.109G>A mutations in the GJB2 gene have been identified as important genetic causes of hearing impairment as they accounted for the majority of mutations in deaf Caucasians.

Figure 4B:
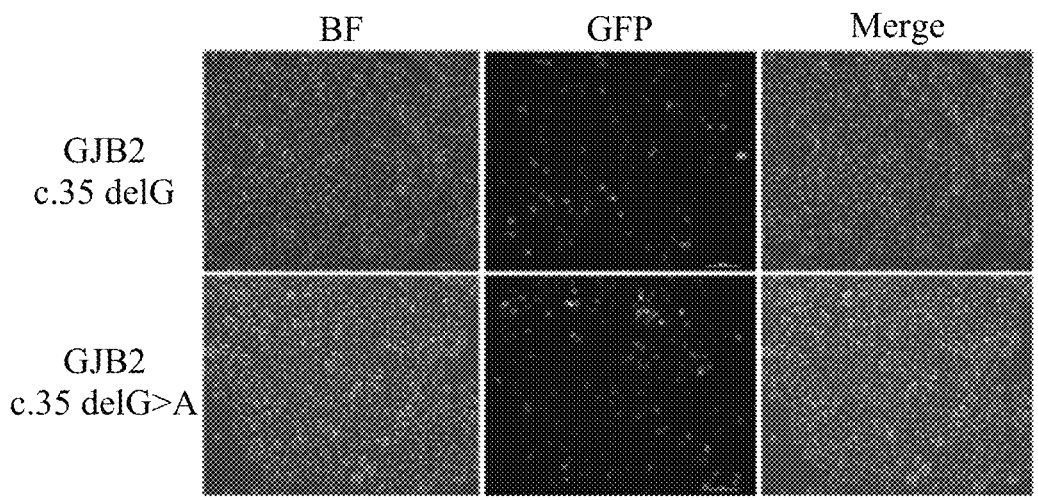
FIG. 4B is a result chart of human HEK293T cells co-transfected with plasmid pAB-mCherry and GJB2-EX35-AF or GJB2-EX109-AF for 48 hours. HEK293T cells with eGFP green fluorescence were observed. Scale bar: 100 μm.

GJB2-EX35-AF and GJB2-EX109-AF were respectively transfected along with pAB-mCherry into human HEK293T cells for 48 hours (linear DNA:vector=0.12 μg:1 μg), and the results were observed by fluorescence microscopy. As shown in FIG. 4B, some of HEK293T cells expressed eGFP, which was encoded in the artificial intron of GJB2-EX35-AF and GJB2-EX109-AF and driven by the CMV promoter.

Figure 4C:
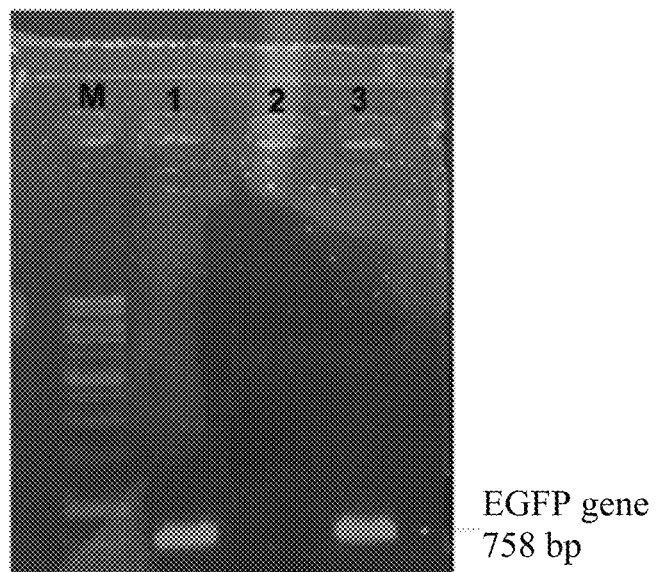
FIG. 4C shows the electrophoresis results of PCR amplification of the EGFP gene from DNA of transfected HEK293T cells of different groups, wherein Lanes M, 1, 2, and 3 represent kb ladder maker, c.35delG group, vehicle control, and c. 109G>A group, respectively.

Furthermore, the PCR amplifying EGFP gene from the genome DNA of transfected HEK293T cells were confirmed by gel electrophoresis. As shown in FIG. 4C, lane 2 of the electrophoresis was vehicle control which did not contain DNA sample, and only lanes 1 and 3 (i.e., the c.35delG and c.109G>A mutations) of the electrophoresis showed EGFP bands, indicating genome editing.

Figure 4D:
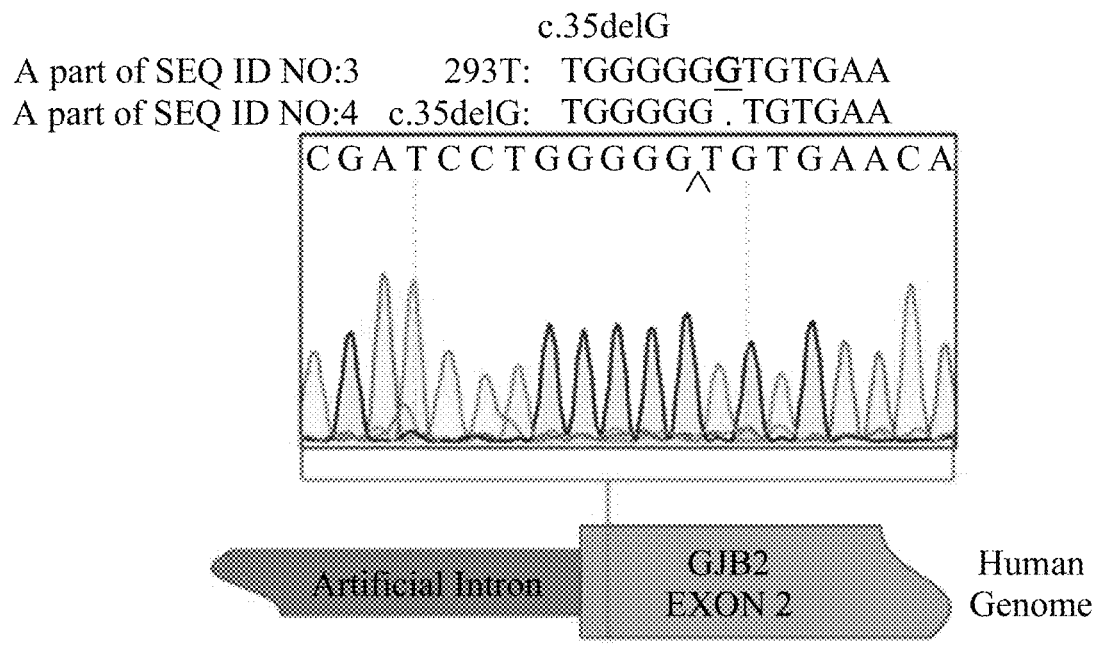
FIGS. 4D and 4E show the sequencing result of Exon 2 of the GJB2 gene from DNA of transfected HEK293T cells of different groups.
Figure 4E:
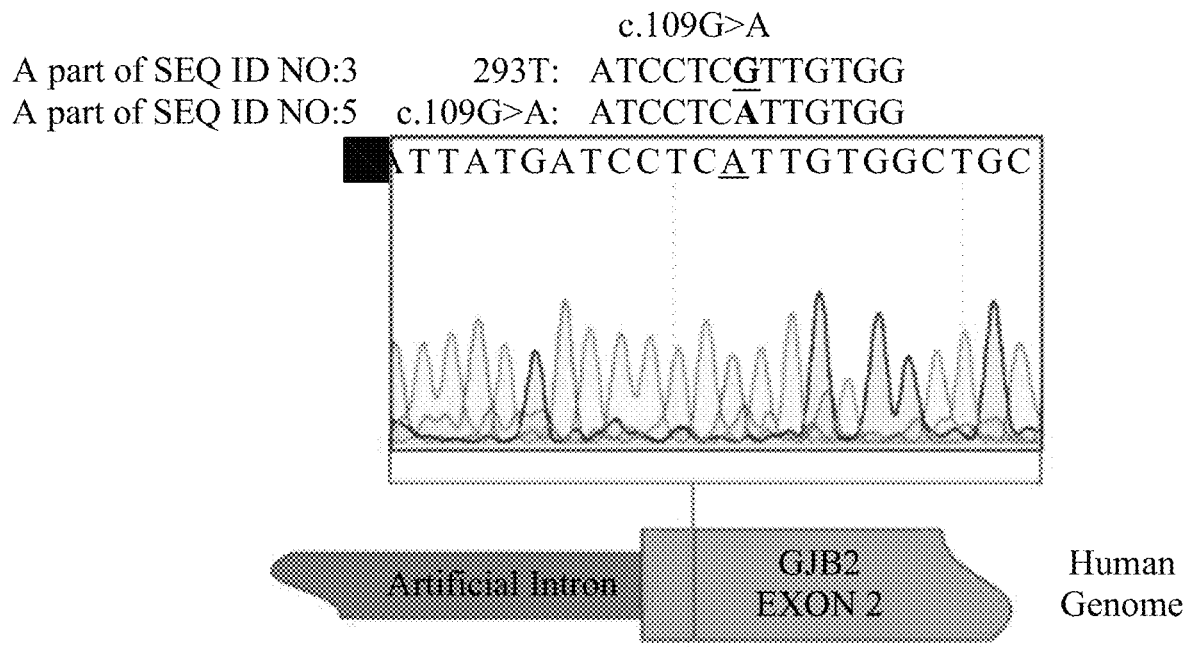

Moreover, the genomic DNA of transfected HEK293T cells was further confirmed by DNA sequencing. Referring to FIGS. 4D and 4E, the sequencing results showed that the genetic change of the GJB2 gene indeed occurred in HEK293T cells transfected with GJB2-EX35-AF or GJB2-EX109-AF.

Therefore, these results indicated the occurrence of recombination between GJB2-EX35-AF and GJB2-EX109-AF and the target locus in human HEK293T cells. Also, these results demonstrated that the present disclosure results in the target replacement of the normal exon by the mutant exon in the human cells. Similarly, it can be understood that the mutated exon in specific diseases can be replaced with the normal exon by using the present disclosure. It is demonstrated that the present disclosure is useful for genome editing and gene therapy.

Example 5: Comparison of Gene Targeting Efficiency of pAB Recombineering System with CRISPR/Cas9n(D10A)

The plasmids for creating c.35 mutation were designed and constructed as pCRISPR/Cas9n(D10A)$^L$ (SEQ ID NO. 27) and pCRISPR/Cas9n(D10A)$^R$ (SEQ ID NO. 28) by Cold Spring Biotech Corp, Taiwan. gRNA of pCRISPR/Cas9n(D10A)$^R$ and pCRISPR/Cas9n(D10A)$^L$ were synthesized and their sequences were represented by SEQ ID NO. 29 and SEQ ID NO. 30, respectively. The c.35delG of GJB2 gene was performed by Cas9 protein with gRNA, expressed from plasmid pCRISPR/Cas9n(D10A)$^R$. A disable plasmid pCRISPR/Cas9n(D10A)$^{DN}$ (SEQ ID NO. 31) as negative control was also constructed by digesting promoter regions with NdeI to inactivate expression of gRNA and cas9 gene.

Human HEK293T cells were treated with vehicle as control or co-transfected with GJB2-EX35-AF and pAB or CRISPR/Cas9n(D10A)$^{R+L}$ for 48 hours. HEK293T cells with GFP expression were then observed and analyzed by flow cytometry. The GFP(+) cells were further analyzed and sorted for evaluating the efficiency of gene targeting.

Figure 5A:
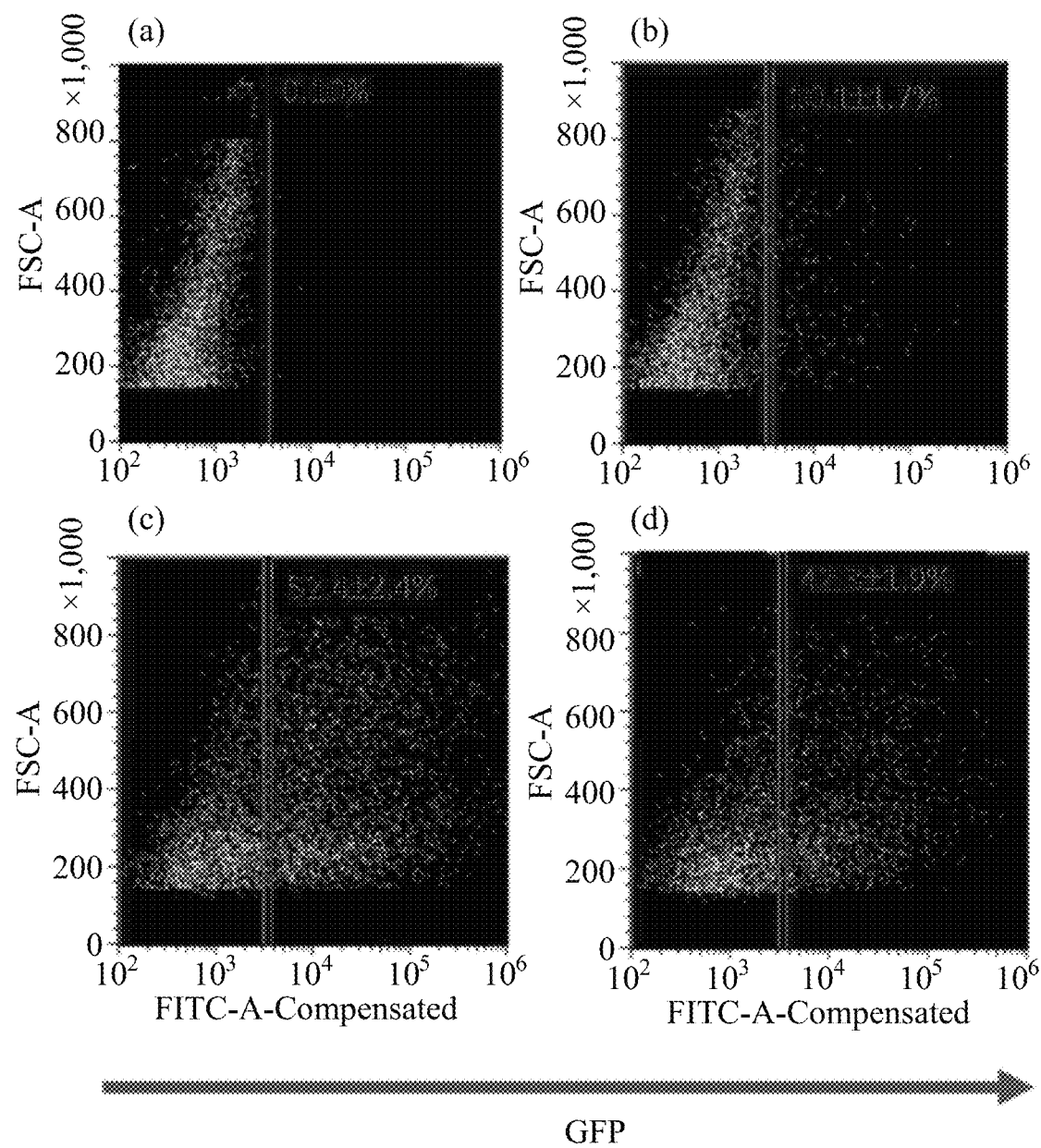
FIGS. 5A and 5B show the comparison of the gene editing efficiency of GJB2 gene c.35 by the method of the present disclosure and CRISPR/Cas9n(D10A) system analyzed by flow cytometry (FIG. 5A) and represented with bar graph (FIG. 5B), wherein (a) is vehicle control, (b) is GJB2-EX35-AF group, (c) is GJB2-EX35-AF+plasmid pAB group, and (d) is GJB2-EX35-AF+CRISPR/Cas9n(D10A)$^{R+L}$ group. Data are presented as mean±sem, **p<0.01 vs. GJB2-EX-AF alone, #p<0.05, n=6.
Figure 5B:
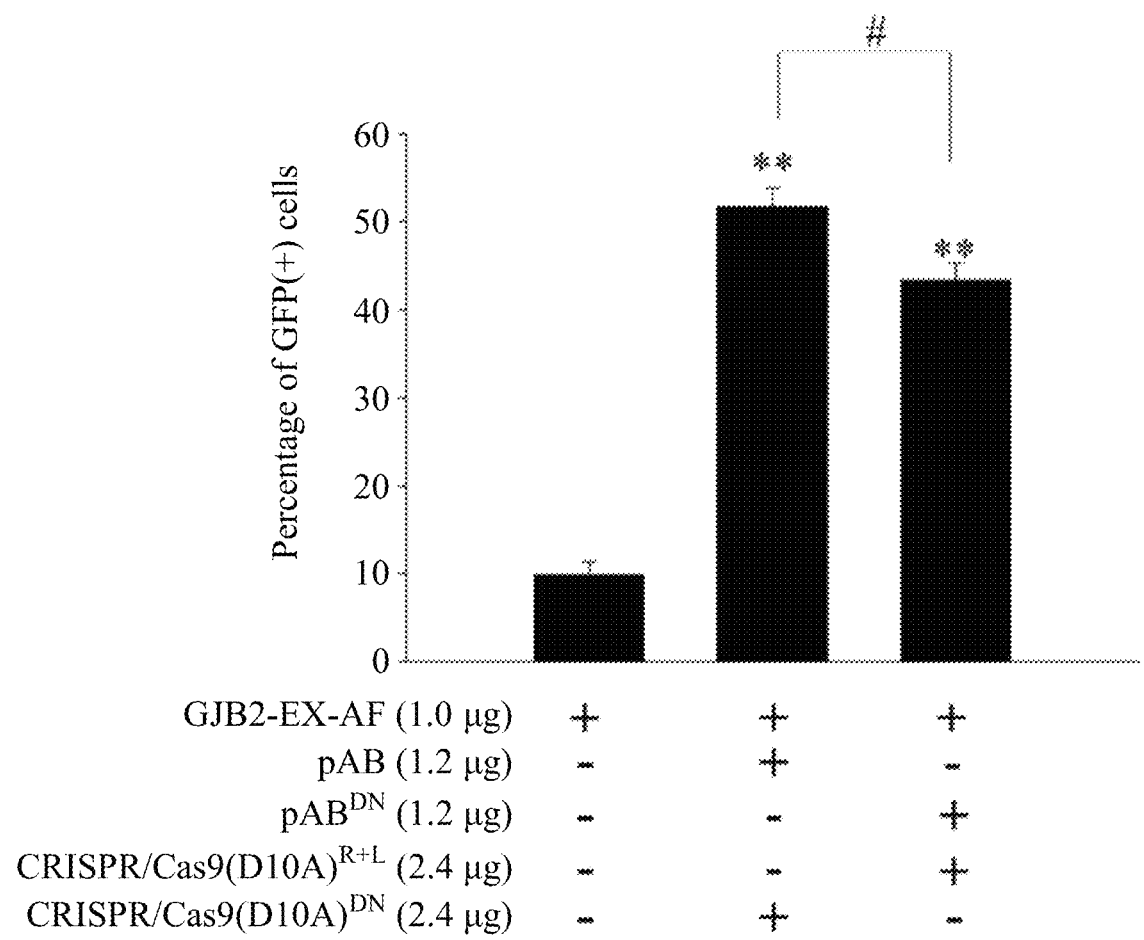

Referring to FIGS. 5A and 5B, the human HEK293T cells were treated with (a) vehicle or with (b) GJB2-EX35-AF, (c) GJB2-EX35-AF and plasmid pAB, (d) GJB2-EX35-AF and CRISPR/Cas9n(D10A)$^{R+L}$, and the gene editing efficiency of GJB2 gene c.35delG mutation by pAB was 52.4%, which was significantly higher as compared to that of CRISPR/Cas9n(D10A) at 42.3%.

By the above Examples, the present disclosure demonstrates the occurrence of lambda Red recombineering between an artificial intron EGFP reporter and the target GJB2 genomic locus in HEK293T cells. The deafness genetic mutations in GJB2 gene, c.35delG and c.109G>A are successfully edited in HEK293T cells through the pAB recombineering system and monitored by the dsDNA/EGFP reporter. The above data suggest that the target replacement of wild-type genomic sequences with the designed mutant genomic sequences in HEK293T cells can be achieved through the pAB recombineering system. The pAB recombineering system of the present disclosure therefore provides an efficient and easily selectable platform for human genome editing by the utilization of dsDNA/EGFP reporter and the combination of FACS system. It can be applied in creating human disease models in vitro and in vivo to facilitate the discovery of disease mechanisms and drug developments. In conclusion, the pAB recombineering system of the present disclosure is promising for precise and efficient human genome targeting/editing not only in the field of basic sciences but also in clinical and regenerative medicine.

The disclosure has been described using exemplary embodiments in detail in the above. However, it is to be understood that the scope of the disclosure is not limited to the disclosed embodiments. On the contrary, it is intended to cover various modifications and similar rearrangement. The scope of the claims therefore should be accorded the broadest interpretation so as to encompass all such modifications and similar arrangements.

What is claimed is:

1. A composition for editing a target nucleic acid sequence, comprising:
one or more nucleic acid molecules each comprising an artificial nucleic acid sequence flanked with capping sequences, wherein each of the capping sequences is homologous to a region in the target nucleic acid sequence, wherein the nucleic acid molecule is a double-stranded DNA, and wherein the artificial nucleic acid sequence is an intron sequence comprising at least one of a splice donor site, a splice acceptor site, a branch site, a selection marker, and any combination thereof, wherein the selection marker comprises a promoter operably linked to a reporter gene to allow a selection for an integrant in genome, and wherein the artificial nucleic acid sequence is removed by RNA splicing during maturation of an RNA product of the target nucleic acid sequence; and
Lambda beta protein or a linear or circular vector comprising a nucleic acid sequence encoding the Lambda beta protein.

2. The composition of claim 1, wherein the promoter is a constitutive promoter, an inducible promoter, or a cell or tissue-specific promoter, and the reporter gene is a fluorescent reporter gene, an enzymatic reporter gene or an antibiotic selection gene.

3. The composition of claim 1, wherein the region in the target nucleic acid sequence is an exon or an intron.

4. The composition of claim 1, further comprising at least one of exonuclease and anti-RecBCD protein.

5. The composition of claim 1, wherein the vector further comprises a promoter operably linked to the nucleic acid sequence encoding Lambda beta protein.

6. The composition of claim 5, wherein the vector further comprises at least one nucleic acid sequence selected from the group consisting of a nucleic acid sequence encoding exonuclease, a nucleic acid sequence encoding anti-RecBCD protein, and a reporter gene.

7. The composition of claim 6, wherein the promoter is a constitutive promoter, an inducible promoter, or a cell or tissue-specific promoter, and the reporter gene is a fluorescent reporter gene, an enzymatic reporter gene or an antibiotic selection gene.

8. The composition of claim 6, wherein the vector, in 5' to 3' downstream direction, comprises the promoter, the nucleic acid sequence encoding Lambda beta protein, the nucleic acid sequence encoding exonuclease, and the reporter gene.

9. The composition of claim 1, wherein the nucleic acid molecule is present in an amount of from 0.05 µg to 5 µg.

10. The composition of claim 1, further comprising at least one system chosen from zinc-finger nuclease (ZFN), transcription activator-like effector nuclease (TALEN) and clustered regularly interspaced short palindromic repeats (CRISPR)/Cas systems.

11. A method for editing a target nucleic acid sequence, comprising:
introducing the composition of claim 1 into a cell for a genetic change in the target nucleic acid sequence to be induced.

12. The method of claim 11, further comprising detecting the cell with the genetic change.

13. The method of claim 11, wherein the editing of the target nucleic acid sequence is at least one selected from the group consisting of recombineering, genome modification, gene knockin, and gene knockout.

14. The method of claim 11, wherein the cell is a eukaryotic cell.

15. The method of claim 14, wherein the eukaryotic cell is a mammalian cell.

16. The method of claim 15, wherein the mammalian cell is a human cell.

\* \* \* \* \*